(12) United States Patent
Childs et al.

(10) Patent No.: US 9,439,693 B2
(45) Date of Patent: Sep. 13, 2016

(54) STEERABLE NEEDLE ASSEMBLY FOR USE IN VERTEBRAL BODY AUGMENTATION

(71) Applicant: DePuy Synthes Products, Inc., Raynham, MA (US)

(72) Inventors: Joseph M. Childs, Middleboro, MA (US); Michael A. Fisher, Lawrenceville, GA (US); Raymond Murphy, Attleboro, MA (US); Christopher Ramsay, West Wareham, MA (US); Paul S. Maguire, Hope Valley, RI (US); Christine Rusbarsky, Norton, MA (US); David Konieczynski, Needham, MA (US); Payman Afshari, South Easton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 422 days.

(21) Appl. No.: 13/756,592

(22) Filed: Feb. 1, 2013

(65) Prior Publication Data
US 2014/0221967 A1    Aug. 7, 2014

(51) Int. Cl.
| | | |
|---|---|---|
| *A61M 25/01* | (2006.01) | |
| *A61B 17/70* | (2006.01) | |
| *A61B 17/88* | (2006.01) | |
| *A61B 17/00* | (2006.01) | |

(52) U.S. Cl.
CPC ....... *A61B 17/7094* (2013.01); *A61B 17/8805* (2013.01); *A61B 2017/00309* (2013.01)

(58) Field of Classification Search
CPC .......... A61B 17/7094; A61B 17/8802; A61B 17/8805; A61B 17/885; A61B 2017/00309; A61B 2017/00314; A61M 25/0136; A61M 25/0138; A61M 2025/0058
See application file for complete search history.

(56) References Cited

U.S. PATENT DOCUMENTS

| | | |
|---|---|---|
| 3,060,972 A | 10/1962 | Sheldon |
| 3,223,083 A | 12/1965 | Cobey |
| 3,266,059 A | 8/1966 | Stelle |
| 3,503,385 A | 3/1970 | Stevens |
| 4,405,249 A | 9/1983 | Scales |

(Continued)

FOREIGN PATENT DOCUMENTS

| | | |
|---|---|---|
| WO | 9613297 | 5/1996 |
| WO | 9620752 | 7/1996 |

(Continued)

OTHER PUBLICATIONS

U.S. Official Action, dated Feb. 25, 2013, received in connection with related U.S. Appl. No. 13/205,826.

(Continued)

*Primary Examiner* — Laura Bouchelle
(74) *Attorney, Agent, or Firm* — Meunier Carlin & Curfman LLC

(57) ABSTRACT

Disclosed herein are devices for minimally invasive vertebral augmentation and restoration of spinal lordosis using a steerable cannula assembly. When deployed, the articulating cannula, including an outer cannula and an inner cannula extending into a central lumen of the outer cannula and coupled to each other at their distal ends, can be manipulated to curve/bend the body of the articulating cannula. This manipulation is used to create a void within the interior body and may also be used to control delivery of a treatment element to the interior body.

20 Claims, 32 Drawing Sheets

(56) References Cited

U.S. PATENT DOCUMENTS

| | | |
|---|---|---|
| 4,616,631 A | 10/1986 | Takahashi |
| 4,627,434 A | 12/1986 | Murray |
| 4,630,616 A | 12/1986 | Tretinyak |
| 4,653,489 A | 3/1987 | Tronzo |
| 4,947,827 A | 8/1990 | Opie et al. |
| 4,969,888 A | 11/1990 | Scholten et al. |
| 4,998,923 A | 3/1991 | Samson et al. |
| 5,002,543 A | 3/1991 | Bradshaw et al. |
| 5,030,201 A | 7/1991 | Palestrant |
| 5,108,404 A | 4/1992 | Scholten et al. |
| 5,231,989 A | 8/1993 | Middleman et al. |
| 5,284,128 A * | 2/1994 | Hart ............................ 600/208 |
| 5,411,514 A | 5/1995 | Fucci et al. |
| 5,438,975 A | 8/1995 | Miyagi et al. |
| 5,488,761 A | 2/1996 | Leone |
| 5,509,923 A | 4/1996 | Middleman et al. |
| 5,512,037 A | 4/1996 | Russell et al. |
| 5,545,200 A | 8/1996 | West et al. |
| 5,709,697 A | 1/1998 | Ratcliff et al. |
| 5,749,828 A | 5/1998 | Solomon et al. |
| 5,749,879 A | 5/1998 | Middleman et al. |
| 5,755,731 A | 5/1998 | Grinberg |
| 5,766,196 A | 6/1998 | Griffiths |
| 5,807,241 A | 9/1998 | Heimberger |
| 5,851,208 A | 12/1998 | Trott |
| 5,851,212 A | 12/1998 | Zirps et al. |
| 5,860,995 A | 1/1999 | Berkelaar |
| 5,873,817 A | 2/1999 | Kokish et al. |
| 5,904,690 A | 5/1999 | Middleman et al. |
| 5,938,678 A | 8/1999 | Zirps et al. |
| 5,972,015 A | 10/1999 | Scribner et al. |
| 5,987,344 A | 11/1999 | West |
| 6,013,024 A | 1/2000 | Mitsuda et al. |
| 6,019,776 A | 2/2000 | Preissman et al. |
| 6,033,411 A | 3/2000 | Preissman |
| 6,048,339 A | 4/2000 | Zirps et al. |
| 6,048,346 A | 4/2000 | Reiley et al. |
| 6,053,907 A | 4/2000 | Zirps |
| 6,053,922 A | 4/2000 | Krause et al. |
| 6,077,287 A | 6/2000 | Taylor et al. |
| 6,099,514 A | 8/2000 | Sharkey et al. |
| 6,217,581 B1 | 4/2001 | Tolson |
| 6,231,615 B1 | 5/2001 | Preissman |
| 6,241,734 B1 | 6/2001 | Scribner et al. |
| 6,248,110 B1 | 6/2001 | Reiley et al. |
| 6,280,456 B1 | 8/2001 | Scribner et al. |
| 6,309,420 B1 | 10/2001 | Preissman |
| 6,337,142 B2 | 1/2002 | Harder et al. |
| 6,348,055 B1 | 2/2002 | Preissman |
| 6,364,828 B1 | 4/2002 | Yeung et al. |
| 6,375,659 B1 | 4/2002 | Erbe et al. |
| 6,383,190 B1 | 5/2002 | Preissman |
| 6,395,007 B1 | 5/2002 | Bhatnagar et al. |
| 6,402,758 B1 | 6/2002 | Tolson |
| 6,440,138 B1 | 8/2002 | Reiley et al. |
| 6,450,948 B1 | 9/2002 | Matsuura et al. |
| 6,491,626 B1 | 12/2002 | Stone et al. |
| 6,582,446 B1 | 6/2003 | Marchosky |
| 6,613,054 B2 | 9/2003 | Scribner et al. |
| RE38,335 E | 11/2003 | Aust et al. |
| 6,641,587 B2 | 11/2003 | Scribner et al. |
| 6,645,213 B2 | 11/2003 | Sand et al. |
| 6,656,195 B2 | 12/2003 | Peters et al. |
| 6,676,664 B1 | 1/2004 | Al-Assir |
| 6,679,886 B2 | 1/2004 | Weikel et al. |
| 6,716,216 B1 | 4/2004 | Boucher et al. |
| 6,719,761 B1 | 4/2004 | Reiley et al. |
| 6,726,691 B2 | 4/2004 | Osorio et al. |
| 6,730,095 B2 | 5/2004 | Olson, Jr. et al. |
| 6,740,093 B2 | 5/2004 | Hochschuler et al. |
| 6,743,239 B1 | 6/2004 | Kuehn et al. |
| 6,746,451 B2 | 6/2004 | Middleton et al. |
| 6,770,079 B2 | 8/2004 | Bhatnagar et al. |
| 6,783,515 B1 | 8/2004 | Miller et al. |
| 6,814,736 B2 | 11/2004 | Reiley et al. |
| 6,863,672 B2 | 3/2005 | Reiley et al. |
| 6,875,170 B2 | 4/2005 | Francois et al. |
| 6,875,219 B2 | 4/2005 | Arramon et al. |
| 6,887,246 B2 | 5/2005 | Bhatnagar et al. |
| 6,923,813 B2 | 8/2005 | Phillips et al. |
| 7,048,743 B2 | 5/2006 | Miller et al. |
| RE39,152 E | 6/2006 | Aust et al. |
| 7,066,942 B2 | 6/2006 | Treace |
| 7,153,306 B2 | 12/2006 | Ralph et al. |
| 7,153,307 B2 | 12/2006 | Scribner et al. |
| 7,250,027 B2 | 7/2007 | Barry |
| 7,252,671 B2 | 8/2007 | Scribner et al. |
| 7,264,622 B2 | 9/2007 | Michelson |
| 7,326,176 B2 | 2/2008 | Machiya et al. |
| 7,402,151 B2 * | 7/2008 | Rosenman ........ A61M 25/0045 604/510 |
| 7,476,226 B2 | 1/2009 | Weikel et al. |
| 7,503,920 B2 | 3/2009 | Siegal |
| 7,510,579 B2 | 3/2009 | Preissman |
| 7,544,196 B2 | 6/2009 | Bagga et al. |
| 7,559,932 B2 | 7/2009 | Truckai et al. |
| 7,572,263 B2 | 8/2009 | Preissman |
| 7,585,300 B2 | 9/2009 | Cha |
| 7,591,783 B2 | 9/2009 | Boulais et al. |
| 7,591,822 B2 | 9/2009 | Olson, Jr. et al. |
| 7,641,664 B2 | 1/2010 | Pagano |
| 7,666,205 B2 | 2/2010 | Weikel et al. |
| 7,704,256 B2 | 4/2010 | Sand et al. |
| 7,713,273 B2 | 5/2010 | Krueger et al. |
| 7,731,720 B2 | 6/2010 | Sand et al. |
| 7,842,041 B2 | 11/2010 | Liu et al. |
| 7,874,980 B2 | 1/2011 | Sonnenschein et al. |
| 7,879,038 B2 | 2/2011 | Reiley et al. |
| 7,909,827 B2 | 3/2011 | Reiley et al. |
| 7,947,000 B2 | 5/2011 | Vargas et al. |
| 8,080,061 B2 | 12/2011 | Appenzeller et al. |
| 8,123,750 B2 | 2/2012 | Norton et al. |
| 8,157,806 B2 | 4/2012 | Frigg et al. |
| 8,221,424 B2 | 7/2012 | Cha |
| 8,246,622 B2 | 8/2012 | Siegal et al. |
| 8,246,637 B2 | 8/2012 | Viola et al. |
| 8,262,563 B2 | 9/2012 | Bakos et al. |
| 8,303,594 B2 | 11/2012 | Lynch et al. |
| 8,322,469 B2 | 12/2012 | Yoon et al. |
| 8,348,950 B2 | 1/2013 | Assell et al. |
| 8,419,747 B2 | 4/2013 | Hinman et al. |
| 8,454,631 B2 | 6/2013 | Viola et al. |
| 8,475,453 B2 | 7/2013 | Marczyk et al. |
| 8,495,934 B2 | 7/2013 | Schneider et al. |
| 8,496,674 B2 | 7/2013 | Cabrera et al. |
| 9,119,639 B2 | 9/2015 | Kuntz |
| 2001/0049531 A1 | 12/2001 | Reiley et al. |
| 2002/0026197 A1 | 2/2002 | Foley et al. |
| 2002/0082605 A1 | 6/2002 | Reiley et al. |
| 2002/0151927 A1 | 10/2002 | Douk et al. |
| 2002/0188299 A1 | 12/2002 | Reiley et al. |
| 2002/0188300 A1 | 12/2002 | Arramon et al. |
| 2003/0004537 A1 | 1/2003 | Boyle et al. |
| 2003/0036763 A1 | 2/2003 | Bhatnagar et al. |
| 2003/0163085 A1 | 8/2003 | Tanner et al. |
| 2003/0187445 A1 | 10/2003 | Keith et al. |
| 2003/0187449 A1 | 10/2003 | McCleary et al. |
| 2003/0191474 A1 | 10/2003 | Cragg et al. |
| 2004/0024409 A1 | 2/2004 | Sand et al. |
| 2004/0024410 A1 | 2/2004 | Olson, Jr. et al. |
| 2004/0267269 A1 | 12/2004 | Middleton et al. |
| 2005/0070912 A1 | 3/2005 | Voellmicke |
| 2005/0070913 A1 * | 3/2005 | Milbocker et al. ............. 606/92 |
| 2005/0075538 A1 | 4/2005 | Banik et al. |
| 2005/0228397 A1 | 10/2005 | Malandain et al. |
| 2005/0240193 A1 | 10/2005 | Layne et al. |
| 2005/0256452 A1 * | 11/2005 | DeMarchi ........ A61M 25/0017 604/95.04 |
| 2005/0272978 A1 | 12/2005 | Brunnen et al. |
| 2006/0100640 A1 | 5/2006 | Bolduc |
| 2006/0116689 A1 | 6/2006 | Albans et al. |
| 2006/0116690 A1 | 6/2006 | Pagano |
| 2006/0142694 A1 | 6/2006 | Bednarek et al. |
| 2006/0167416 A1 | 7/2006 | Mathis et al. |

(56) References Cited

U.S. PATENT DOCUMENTS

| | | |
|---|---|---|
| 2006/0178560 A1 | 8/2006 | Saadat et al. |
| 2007/0043430 A1 | 2/2007 | Stinson |
| 2007/0055279 A1 | 3/2007 | Sand et al. |
| 2007/0055284 A1 | 3/2007 | Osorio et al. |
| 2007/0055285 A1 | 3/2007 | Osorio et al. |
| 2007/0093840 A1 | 4/2007 | Pacelli et al. |
| 2007/0118142 A1 | 5/2007 | Krueger et al. |
| 2007/0118143 A1 | 5/2007 | Ralph et al. |
| 2007/0142842 A1 | 6/2007 | Krueger et al. |
| 2007/0179340 A1 | 8/2007 | Jorgensen |
| 2007/0198020 A1 | 8/2007 | Reiley et al. |
| 2007/0198023 A1 | 8/2007 | Sand et al. |
| 2008/0058827 A1 | 3/2008 | Osorio et al. |
| 2008/0065020 A1 | 3/2008 | Ralph et al. |
| 2008/0065087 A1 | 3/2008 | Osorio et al. |
| 2008/0065190 A1 | 3/2008 | Osorio et al. |
| 2008/0086142 A1 | 4/2008 | Kohm et al. |
| 2008/0091170 A1 | 4/2008 | Vargas et al. |
| 2008/0140079 A1 | 6/2008 | Osorio et al. |
| 2008/0188854 A1 | 8/2008 | Moser |
| 2008/0188928 A1 | 8/2008 | Salahieh et al. |
| 2008/0200915 A1 | 8/2008 | Globerman et al. |
| 2008/0208255 A1 | 8/2008 | Siegal |
| 2008/0228192 A1 | 9/2008 | Beyar et al. |
| 2008/0228195 A1 | 9/2008 | von Jako et al. |
| 2008/0269766 A1 | 10/2008 | Justis |
| 2008/0269796 A1 | 10/2008 | Reiley et al. |
| 2008/0287741 A1 | 11/2008 | Ostrovsky et al. |
| 2009/0069850 A1 | 3/2009 | Fuerderer |
| 2009/0076511 A1 | 3/2009 | Osman |
| 2009/0076517 A1 | 3/2009 | Reiley et al. |
| 2009/0099420 A1 | 4/2009 | Woodley et al. |
| 2009/0124857 A1 | 5/2009 | Viola |
| 2009/0131850 A1 | 5/2009 | Geiger |
| 2009/0131886 A1 | 5/2009 | Liu et al. |
| 2009/0131945 A1 | 5/2009 | Liu et al. |
| 2009/0131948 A1* | 5/2009 | Liu et al. .................. 606/93 |
| 2009/0156995 A1 | 6/2009 | Martin et al. |
| 2009/0157060 A1 | 6/2009 | Teague et al. |
| 2009/0292289 A9 | 11/2009 | Sand et al. |
| 2009/0299282 A1 | 12/2009 | Lau et al. |
| 2009/0306587 A1 | 12/2009 | Milijasevic et al. |
| 2009/0326326 A1 | 12/2009 | Lin et al. |
| 2009/0326538 A1 | 12/2009 | Sennett et al. |
| 2010/0010298 A1 | 1/2010 | Bakos et al. |
| 2010/0010299 A1 | 1/2010 | Bakos et al. |
| 2010/0036202 A1 | 2/2010 | Lin et al. |
| 2010/0042104 A1 | 2/2010 | Kota et al. |
| 2010/0048999 A1 | 2/2010 | Boulais et al. |
| 2010/0057087 A1 | 3/2010 | Cha |
| 2010/0076265 A1 | 3/2010 | Yamakawa et al. |
| 2010/0076266 A1 | 3/2010 | Boulais et al. |
| 2010/0076433 A1 | 3/2010 | Taylor et al. |
| 2010/0082033 A1 | 4/2010 | Germain |
| 2010/0094269 A1 | 4/2010 | Pellegrino et al. |
| 2010/0100098 A1 | 4/2010 | Norton et al. |
| 2010/0114098 A1 | 5/2010 | Carl |
| 2010/0121336 A1 | 5/2010 | Linderman et al. |
| 2010/0130823 A1 | 5/2010 | Ando |
| 2010/0130924 A1 | 5/2010 | Martin et al. |
| 2010/0160736 A1 | 6/2010 | Padget et al. |
| 2010/0160923 A1 | 6/2010 | Sand et al. |
| 2010/0168519 A1 | 7/2010 | Matsuo |
| 2010/0191058 A1 | 7/2010 | Yamazaki |
| 2010/0241123 A1 | 9/2010 | Middleton et al. |
| 2010/0262075 A1 | 10/2010 | Danitz et al. |
| 2010/0268234 A1 | 10/2010 | Aho et al. |
| 2010/0312056 A1 | 12/2010 | Galperin et al. |
| 2010/0331776 A1* | 12/2010 | Salahieh ........... A61M 25/0136 604/95.04 |
| 2011/0009695 A1 | 1/2011 | Lee |
| 2011/0034772 A1 | 2/2011 | Konstorum |
| 2011/0095049 A1 | 4/2011 | Eichholz |
| 2011/0208194 A1 | 8/2011 | Steiner et al. |
| 2011/0218538 A1 | 9/2011 | Sherman et al. |
| 2011/0251615 A1 | 10/2011 | Truckai et al. |
| 2011/0282149 A1 | 11/2011 | Vargas et al. |
| 2011/0295065 A1 | 12/2011 | Gurusamy et al. |
| 2011/0319896 A1 | 12/2011 | Papenfuss et al. |
| 2011/0319898 A1 | 12/2011 | O'Neil et al. |
| 2012/0016367 A1 | 1/2012 | Chabansky et al. |
| 2012/0071876 A1 | 3/2012 | Stoll et al. |
| 2012/0095517 A1 | 4/2012 | Müller et al. |
| 2012/0130381 A1 | 5/2012 | Germain |
| 2012/0191094 A1 | 7/2012 | Alain et al. |
| 2012/0203231 A1 | 8/2012 | Long et al. |
| 2012/0226301 A1 | 9/2012 | Geist |
| 2013/0041377 A1 | 2/2013 | Kuntz |
| 2013/0274784 A1* | 10/2013 | Lenker et al. ................. 606/185 |

FOREIGN PATENT DOCUMENTS

| | | |
|---|---|---|
| WO | 98/17190 | 4/1998 |
| WO | 98/56299 | 12/1998 |
| WO | 99/49819 | 10/1999 |
| WO | 0203870 A1 | 1/2002 |
| WO | 2005/051212 | 6/2005 |
| WO | 2006/050445 | 5/2006 |
| WO | 2007/036815 | 4/2007 |
| WO | 2007/147591 | 12/2007 |
| WO | 2008/011262 | 1/2008 |
| WO | 2012/151396 | 11/2012 |

OTHER PUBLICATIONS

European Search Report from corresponding application No. 14150828.3-1506, dated Apr. 25, 2014.

\* cited by examiner

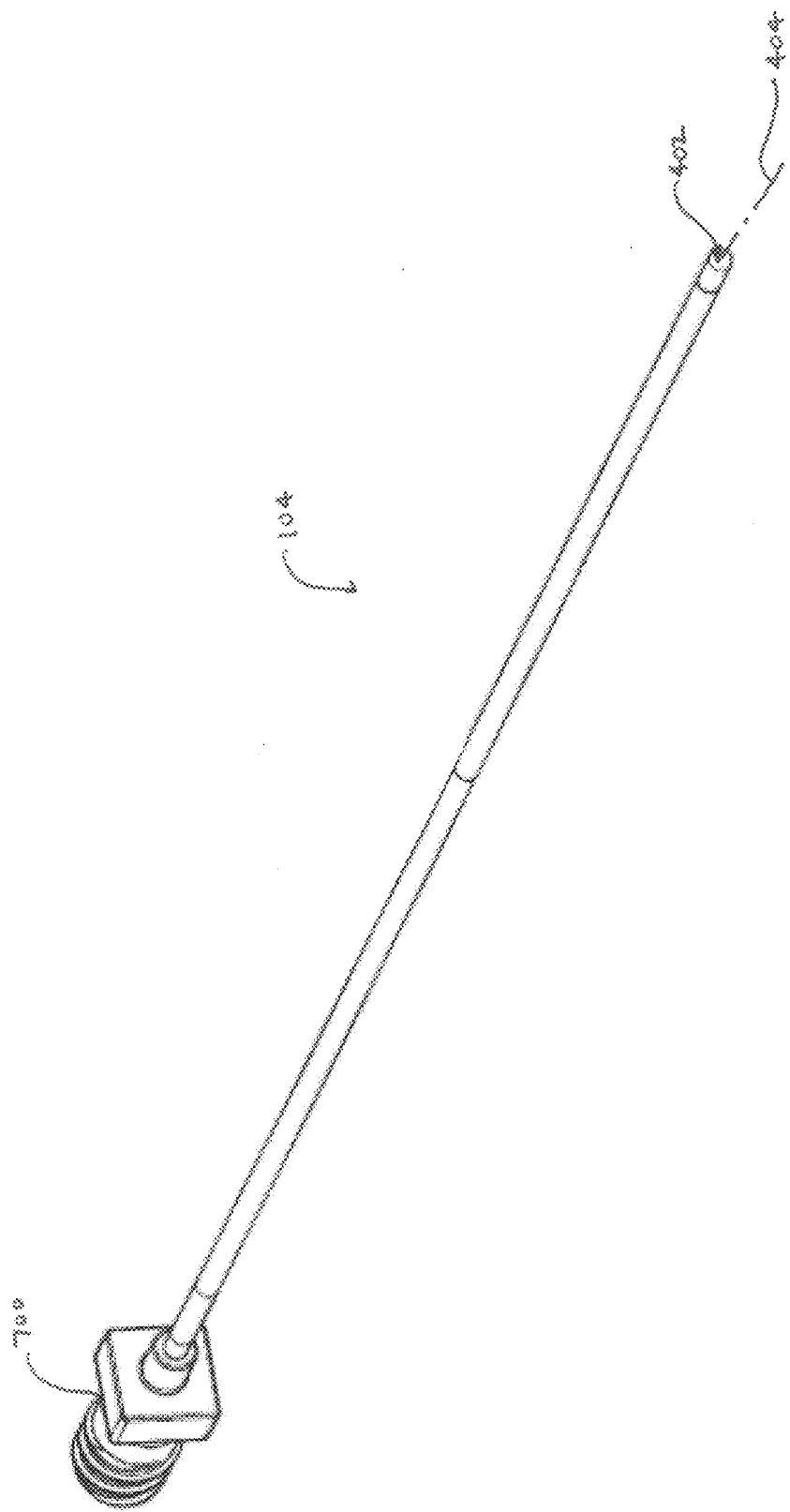

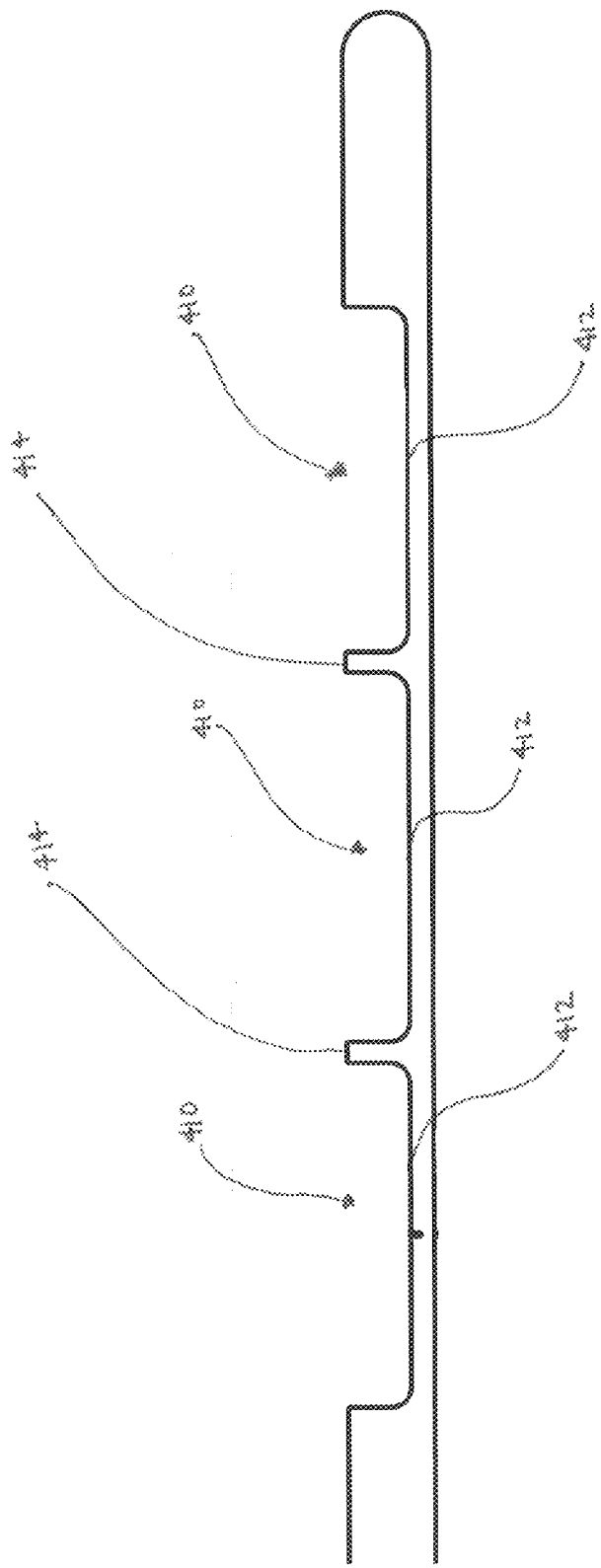

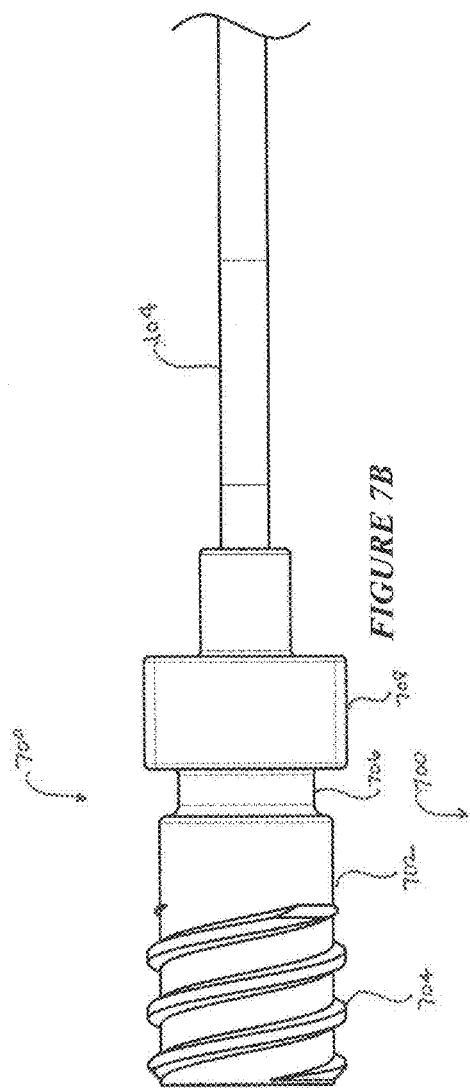
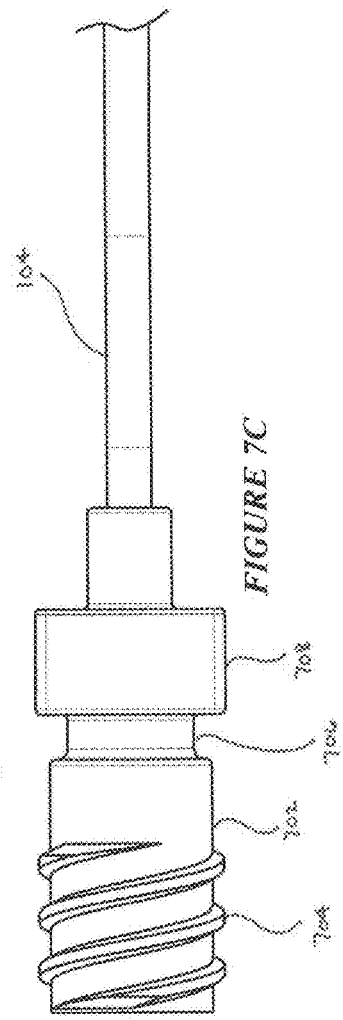
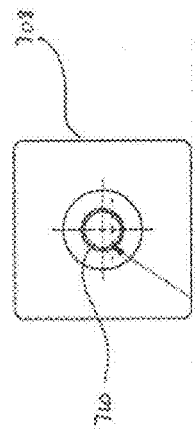
FIGURE 7B
FIGURE 7C
FIGURE 7D

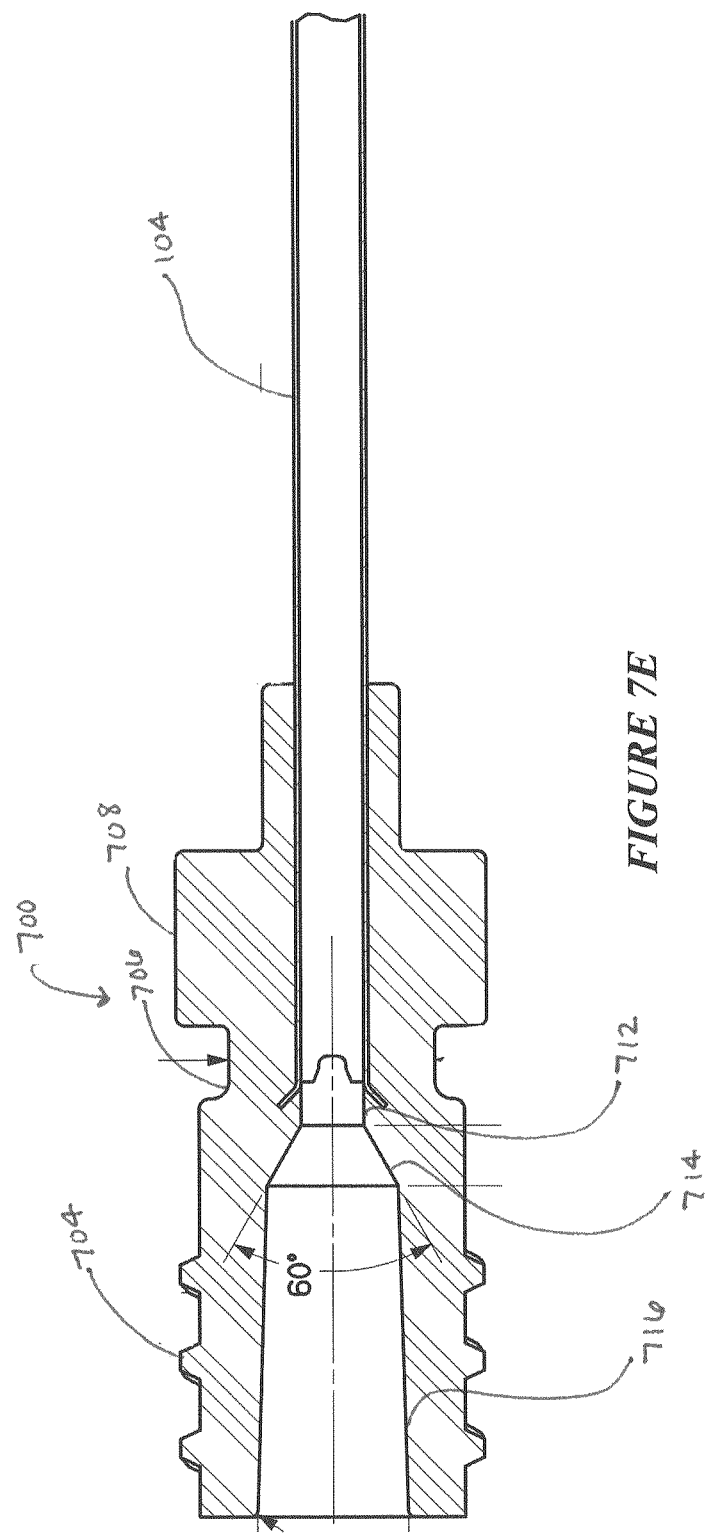

STEERABLE NEEDLE ASSEMBLY FOR USE IN VERTEBRAL BODY AUGMENTATION

TECHNICAL FIELD

This invention relates to a minimally invasive apparatus and method for treating a damaged vertebral body and restoring spinal lordosis.

BACKGROUND

Certain diagnostic and therapeutic procedures require access to and/or formation of a cavity in an interior body region. These procedures can be used to treat cortical bone which, due to osteoporosis, avascular necrosis, cancer, or trauma, for example, may be fractured or prone to compression/collapse. Spinal compression fractures and related spinal deformities, if not successfully treated, can lead to deformation of the normal alignment or curvature, e.g., lordosis, of the affected area of the spine, as well as chronic complications and an overall adverse impact upon the quality of life for the patient. Until recently, doctors were limited to treating such compression fractures and related deformities with pain medications, bed rest, bracing or invasive spinal surgery.

More recently, minimally invasive surgical procedures for treating vertebral compression fractures have been developed. These procedures generally involve the insertion of a rigid cannula, needle or trocar into the interior of a collapsed or otherwise damaged vertebra. The cannula usually includes a lumen or central passage through which another tool, implant or filler material is passed in order to reposition and/or augment the vertebral body.

The most basic of these procedures is vertebroplasty. Vertebroplasty involves injecting a medical-grade bone cement (such as polymethylmethacrylate, a.k.a., PMMA) via a special bone needle into a fractured vertebra. The bone cement is injected with sufficient pressure to compress and displace cancellous bone tissue. However, the direction and containment of the injected cement can be difficult to control because the space the bone cement occupies is ill-defined, self-forming, and highly-dependent upon the internal composition of the cancellous bone. Additionally, vertebroplasty does not always reposition the fractured bone and therefore may not address the problem of spinal deformity due to fracture.

A number of more advanced treatments for vertebral compression fractures are known, and generally involve two phases: (1) reposition, or restoration of the original height of the vertebral body and consequent lordotic correction of the spinal curvature; and (2) augmentation, or addition of material to support or strengthen the fractured bone. As with vertebroplasty, such procedures generally involve use of a cannula, catheter, needle, trocar or other introducer to provide access to the interior of the effected vertebral body.

Procedures, such as kyphoplasty, provide better bounding and control over injected bone cement, other procedures utilize devices for first forming cavities within the cancellous bone (and, accordingly, other interior body regions) prior to injecting bone cement into such a cavity. During balloon kyphoplasty (Kyphon, Inc.), an expandable body or balloon is deployed into the interior body region to form a cavity in, for example, cancellous bone tissue surrounded by fractured cortical bone. Kyphoplasty then achieves the reconstruction of the lordosis, or normal curvature, by inflating the balloon, which expands within the vertebral body restoring it to its original height. These expandable body devices effectively compress and displace the cancellous bone to form an interior cavity that then receives a filling material intended to provide renewed interior structural support for cortical bone.

A common drawback of most systems for repositioning and augmenting damaged vertebrae is that they involve the use of relatively complex apparatus introduced through rigid introducers. These introducers provide little tactile feedback and directional control to the surgeon. Accordingly, there remains a need in the art to provide safe and effective apparatus and methods for minimally invasive repositioning of and osteopathic augmentation of vertebral bodies to restore lordosis of the spine.

SUMMARY

Presented are systems and methods for minimally invasive vertebral augmentation and restoration of spinal lordosis. An aspect of the present disclosure is directed to a steerable cannula assembly. The steerable cannula assembly may comprise an outer cannula and inner cannula. The outer cannula may have a central lumen extending therethrough. The outer cannula may also include an articulating portion that curves in response to a force applied to a proximal end of the outer cannula. The inner cannula may include a central lumen extending therethrough. The inner cannula may be sized and configured to extend into a portion of the central lumen of the outer cannula and be coupled to a distal end of the outer cannula.

Another aspect of the present disclosure is directed to a method for treating a body using a steerable cannula assembly. The method may include inserting an articulating cannula into an interior body, the articulating cannula may include an outer cannula and an inner cannula extending into a central lumen of the outer cannula, the outer cannula coupled the inner cannula at a distal end. The method may further include selectively adjusting the articulating cannula to cause a portion of the articulating cannula to curve, augmenting the interior body, and withdrawing the articulating cannula from the interior body.

The details of one or more embodiments of the invention are set forth in the accompanying drawings and the description below. Other features, objects, and advantages of the invention will be apparent from the description and drawings, and from the claims.

DESCRIPTION OF DRAWINGS

The device is explained in even greater detail in the following drawings. The drawings are merely examples to illustrate the structure of preferred devices and certain features that may be used singularly or in combination with other features. The invention should not be limited to the examples shown.

FIG. 4D is a perspective view of an example inner cannula coupled to a connector;

FIG. 4G is a partial view of an example inner cannula;

FIG. 7B is a top view of an example connector;

FIG. 7C is a side view of an example connector;

FIG. 7D is an end view of an example connector;

FIG. 7E is a cross-section view of an example connector;

DETAILED DESCRIPTION

Figure 1:
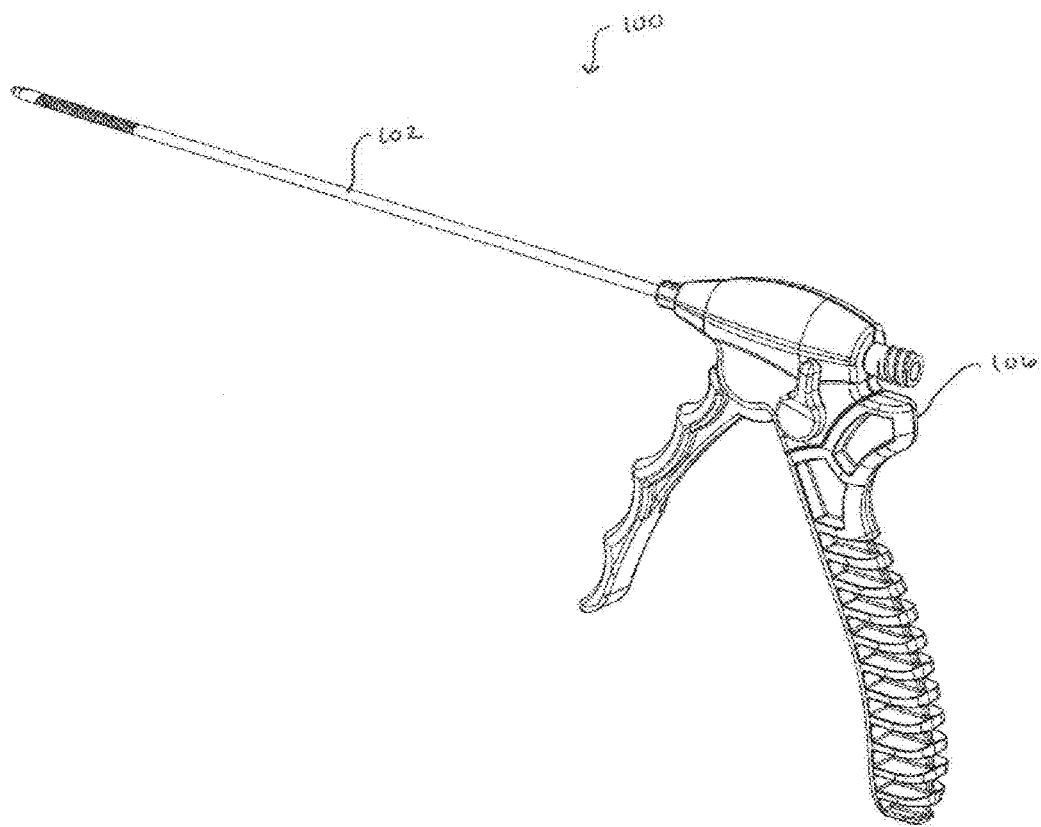
FIG. 1 is a perspective view of an example steerable cannula assembly.

Certain terminology is used in the following description for convenience only and is not limiting. The words "right", "left", "lower", and "upper" designate direction in the drawings to which reference is made. The words "inner", "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The words "anterior", "posterior", "superior", "inferior", "medial", "lateral", and related words and/or phrases designate preferred positions and orientation in the human body to which reference is made. The terminology includes the above-listed words, derivatives thereof, and words of similar import.

In addition, various components may be described herein as extending horizontally along a longitudinal direction "L" and lateral direction "A", and vertically along a transverse direction "T". Unless otherwise specified herein, the terms "lateral", "longitudinal", and "transverse" are used to describe the orthogonal directional components of various items. It should be appreciated that while the longitudinal and lateral directions are illustrated as extending along a horizontal plane, and that the transverse direction is illustrated as extending along a vertical plane, the planes that encompass the various directions may differ during use. Accordingly, the directional terms "vertical" and "horizontal" are used to describe the components merely for the purposes of clarity and illustration and are not meant to be limiting.

Figure 2:
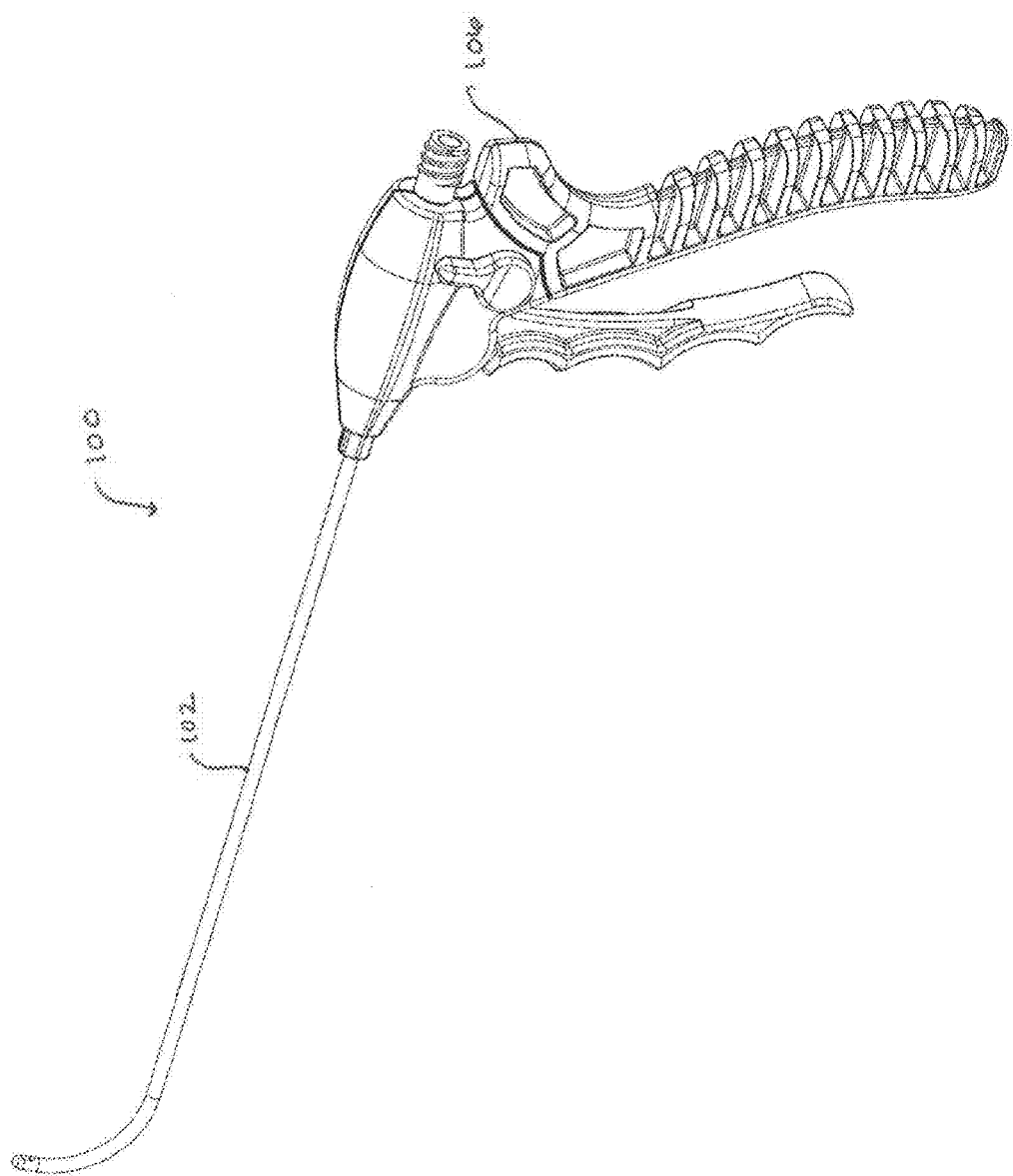
FIG. 2 is a perspective view of an example steerable cannula assembly.

Certain examples of the invention will now be described with reference to the drawings. In general, such embodiments relate to a steerable cannula assembly for providing vertebral body augmentation in situ. FIG. 1 is a perspective view of an example steerable cannula assembly 100. The steerable cannula assembly 100 includes an outer cannula 102 and an inner cannula 104 (not shown). The steerable cannula assembly 100 may also include a handle 106. As illustrated in FIGS. 1 and 2, and as will be described in further detail below, the outer cannula 102 can deflect from a normal, straight, configuration (FIG. 1) to a deflected, curved configuration (FIG. 2).

Figure 3A:
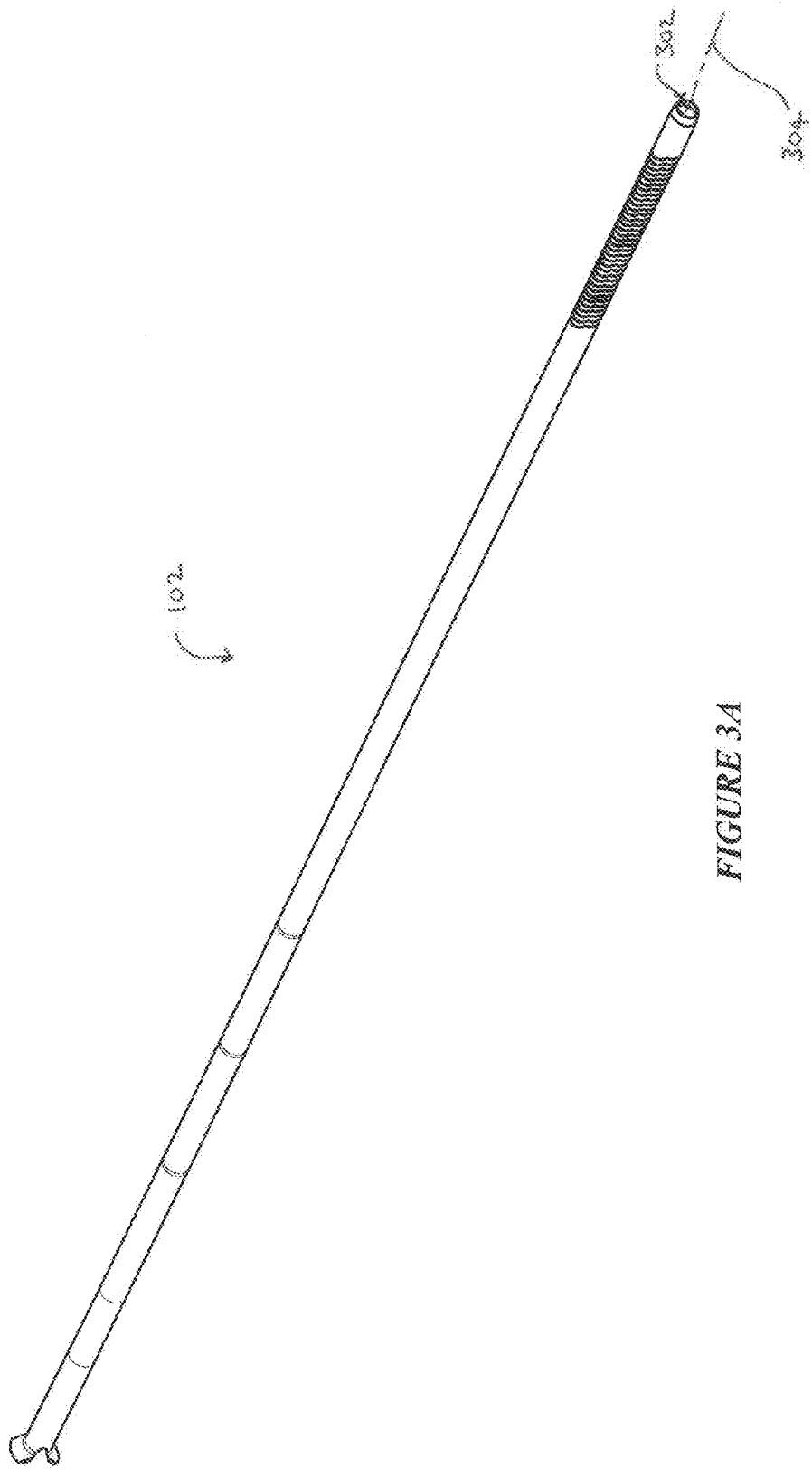
FIG. 3A is a perspective view of an example outer cannula.

FIG. 3A provides a perspective view of an example outer cannula 102. The outer cannula 102 may include a central lumen 302 extending therethrough along the longitudinal axis 304 from the proximate end 306 to the distal end 308.

Figure 3B:
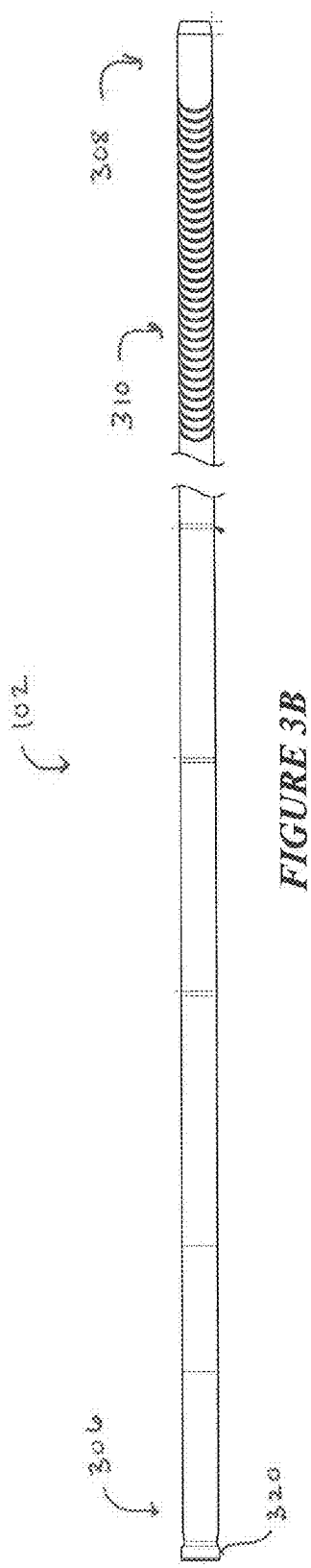
FIG. 3B is a top view of an example outer cannula.
Figure 3C:
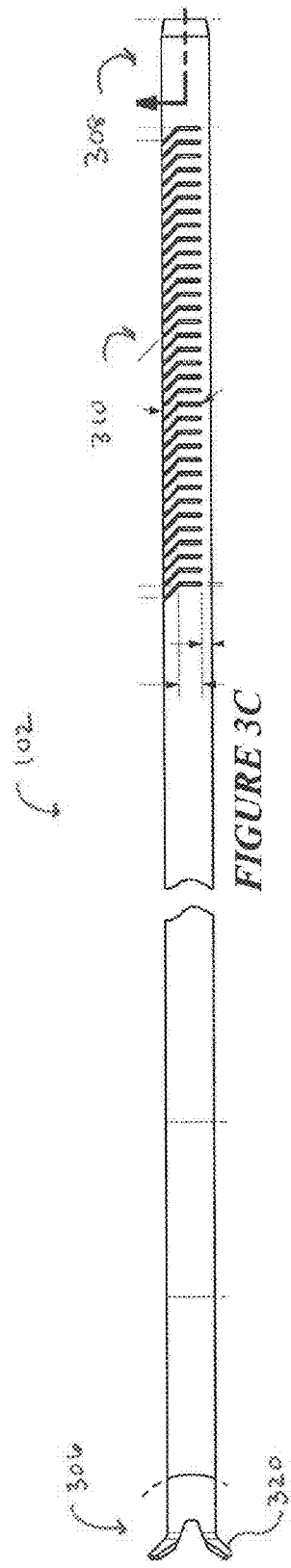
FIG. 3C is a side view of an example outer cannula.

FIGS. 3B and 3C provide a top and side view of the example outer cannula 102. As illustrated, the outer cannula 102 may also include an articulating portion 310. The articulating portion 310 may be located proximate the distal end 308 of the outer cannula 102. In an alternate example, the articulating portion 310 may be located at any portion along outer cannula 102. In another example, the articulating portion 310 may be located at any portion along the outer cannula 102 at any portion so as to aid the performance of a single incision bi-pedicular procedure in a typical vertebral body. The articulating portion 310 may cause a portion of the outer cannula 102 to curve or change shape in response to force applied to the outer cannula 102. For example, the articulating portion 310 may curve in response to a force applied to the proximal end 306 of the outer cannula 102. In another example, the articulating portion 310 may curve in response to a force applied to the distal end 308 of the outer cannula 102. In a further example, the articulating portion 310 may curve in response to a force applied at any portion along the outer cannula 102. The force applied to the outer cannula 102 may be in the direction of the longitudinal axis 304 or in a lateral direction from the longitudinal axis 304. The force may be a compressive, tensile, or sheer force.

Figure 3D:
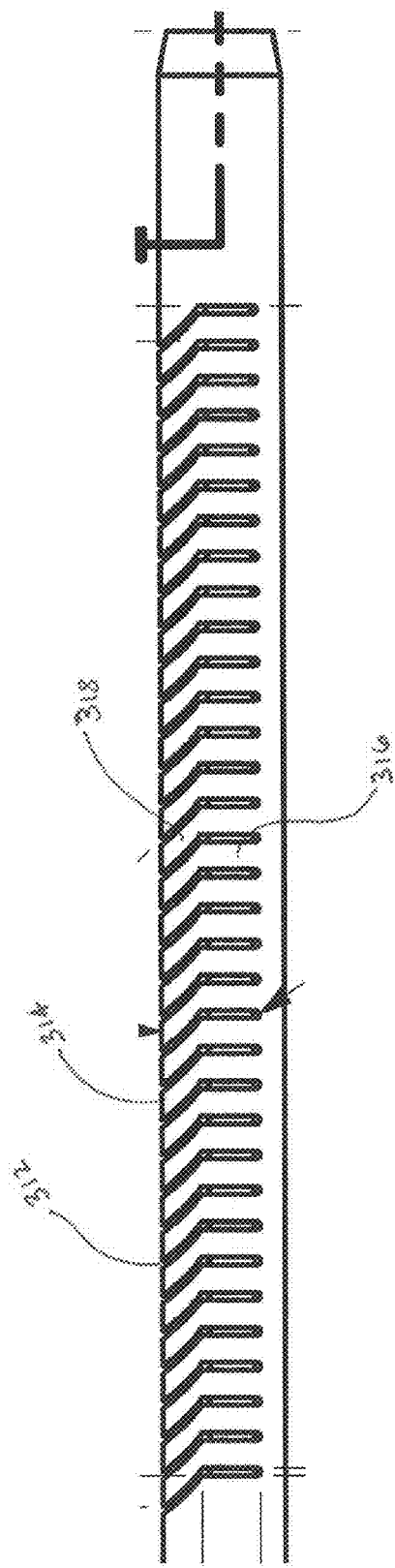
FIG. 3D is a partial view of an example articulating portion of the outer cannula.

The articulating portion 310 may include grooves 312 and corresponding projections 314. The grooves 312 and projections 314 may be sized and configured to interlock when the articulating portion 310 is in a fully curved state. For example, as illustrated in FIG. 3D, the projections 314 may include a vertical portion 316 and an interlocking portion 318. When the articulating portion 310 is in a fully curved state, the projections 314 matingly engage at the interlocking portion 318 such that further motion of the articulating portion 310 is prohibited. It is contemplated that the grooves 312 and corresponding projections 314 located in the articulating portion 310 may define any suitable shape and/or configuration such that they provide the necessary flexation to outer cannula 102. The width of the grooves 312 and the width of the projections 314 can be used to control the articulation angle of the articulating portion 310. For example, the wider the grooves 312 the greater the articulation angle/flexation of the articulating portion 310. The articulation angle/flexation of the articulating portion 310 can be sized and configured to correspond to the articulation angle/flexation necessary to perform a single incision bipedicular procedure in a typical vertebral body.

Figure 3E:
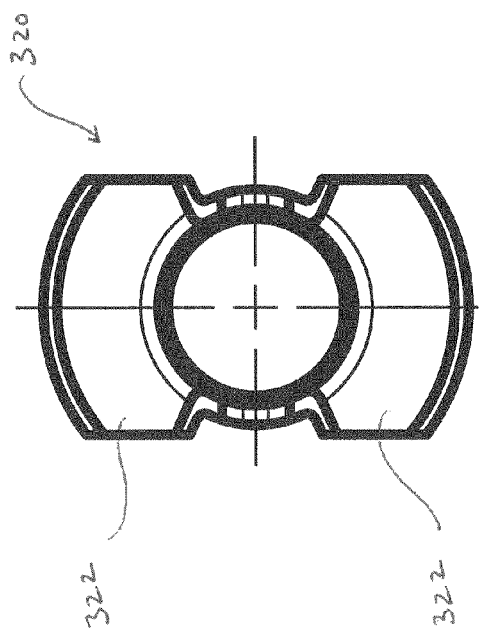
FIG. 3E is an end view of an example outer cannula.
Figure 3F:
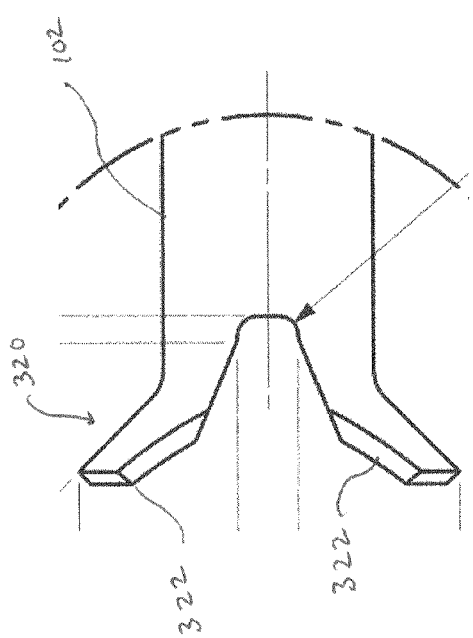
FIG. 3F is a partial end view of an example outer cannula.

The outer cannula 102 may also include an attachment feature 320 for mating with a corresponding connector 600. For example, as illustrated in FIGS. 3E and 3F, the attachment feature 320 may be located at the proximal end 306 of the outer cannula 102 and may include a two projections 322 extending from the outer cannula 102. The projections 322 may be formed from the body surface of the outer cannula 102. In an alternate example, the projections 322 are attached or otherwise joined to the proximal end 306 of the outer cannula 102.

Figure 4A:
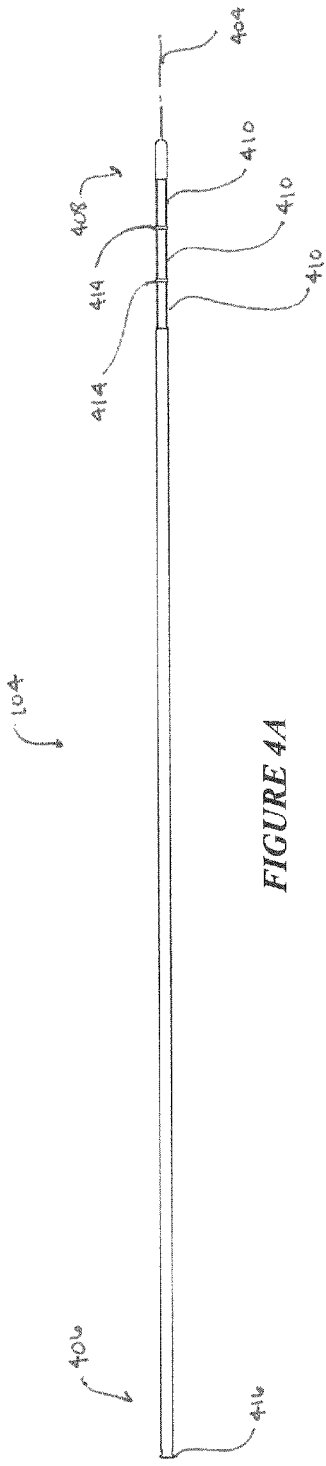
FIG. 4A is a top view of an example inner cannula.
Figure 4B:
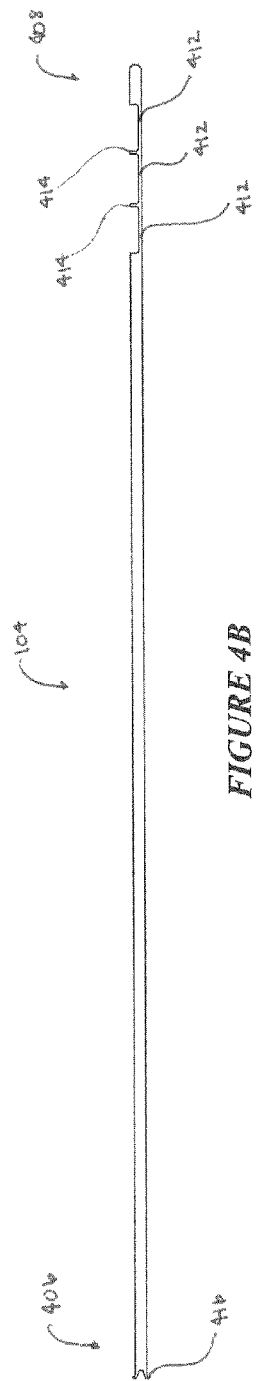
FIG. 4B is a side view of an example inner cannula.
Figure 4C:
FIG. 4C is a bottom view of an example inner cannula.
Figure 4E:
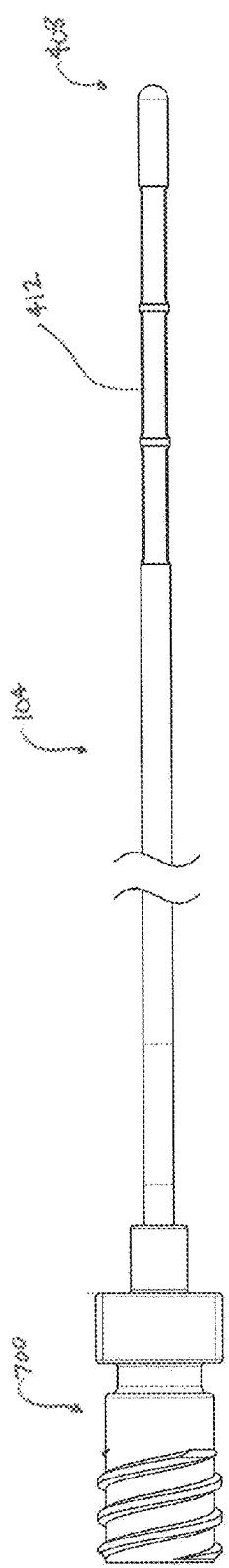
FIG. 4E is a top view of an example inner cannula coupled to a connector.
Figure 4F:
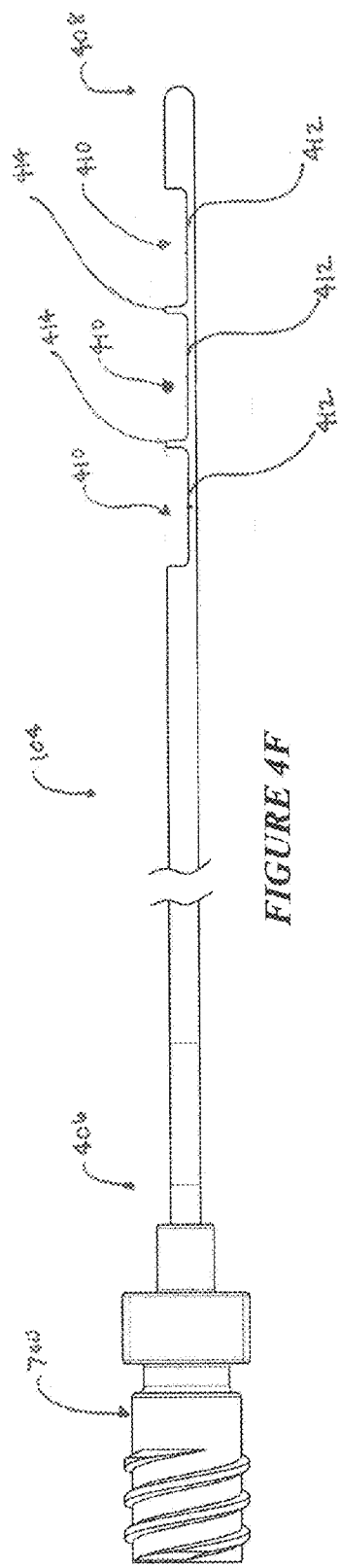
FIG. 4F is a side view of an example inner cannula coupled to a connector.

FIGS. 4A-4C provide top, side and bottom views of an example inner cannula 104, FIG. 4D provides a perspective view of an example inner cannula 104 coupled to a connector 700, and FIGS. 4E and 4F provide top and side views of an example inner cannula 104 coupled to a connector 700. The inner cannula 104 may include a central lumen 402 extending therethrough along the longitudinal axis 404 from the proximate end 406 to the distal end 408. As illustrated, the inner cannula 104 may also include slots 410 extending along the longitudinal axis 404 of the inner cannula 104. The inner cannula 104 can include a single slot 410 or any number of slots 410. As illustrated in FIGS. 4A-4C, 4E and 4F, the inner cannula 104 can include three slots. The size and shape of slots 410 can vary. The slots 410 may include a base portion 412. As illustrated in FIGS. 4A, 4B, 4E and 4F the base 412 may comprise one-quarter the diameter of the inner cannula 104. In another example (not shown), the base 412 may comprise more or less than one-quarter the diameter of the inner cannula 104.

The slots 410 may be located proximate the distal end 408 of the inner cannula 104. In another example, the slots 410 may be located at a portion of the inner cannula 104 that corresponds to the articulating portion 310 on the outer cannula 102 when the inner cannula 104 and the outer cannula 102 are assembled. For example, the total length of the area including the slots 410 along the inner cannula 104 may correspond to the length of the articulating portion 310 along the outer cannula 102. In a further example, the slots 410 may be located at any portion along the inner cannula 104. The slots 410 can be sized, located, and in a quantity to provide flexibility to the inner cannula 104. The slots 410 may cause the inner cannula 104 to curve or otherwise bend in response to a force applied inner cannula 104. For example, the slots 410 may cause the inner cannula 104 to flex in response to a force applied at the proximal end 406 of the inner cannula 104. In another example, the slots 410 may cause the inner cannula 104 to flex in response to a force applied at the distal end 408 of the inner cannula 104. In a further example, the slots 410 cause the inner cannula 104 to flex in response to a force applied at any portion along the inner cannula 104. The force applied to the inner cannula 104 may be in the direction of the longitudinal axis 404 or in a lateral direction from the longitudinal axis 404. The force may be a compressive, tensile, or sheer force.

As illustrated in FIG. 4G, the inner cannula 104 may include support members 414 located between each of the slots 410. The support members 414 may comprise a ring-shaped portion extending in a lateral direction, perpendicular to the longitudinal axis 404 of the inner cannula 104. The support members 414 may include a central lumen (not shown) extending through the body of each of the support members 414. The central lumen 414 may be sized and shape to correspond to the size and shape of the central lumen 402 of the inner cannula 104. In a further embodiment, the central lumen of the support member 414 has a different size and/or shape than the central lumen 402 of the inner cannula 104. As described in more detail below, the support member 414 may prove support for a sealing lumen 500 located between the inner cannula 104 and the outer cannula 102 and thereby prevent the inner lumen 500 from blocking the central lumen 402 of the inner cannula 104.

Figure 4H:
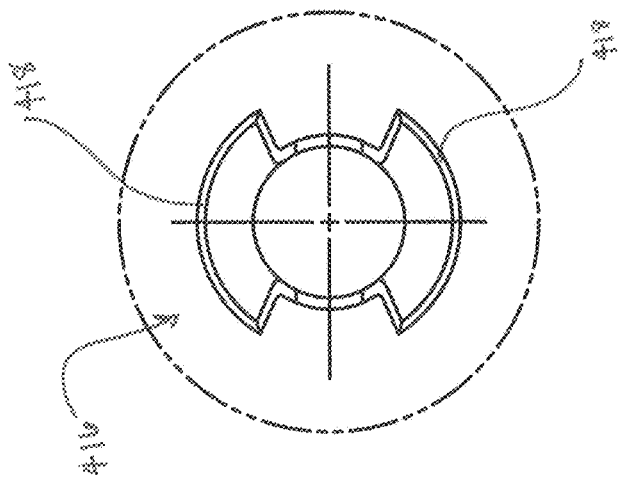
FIG. 4H end view of an example inner cannula.
Figure 4I:
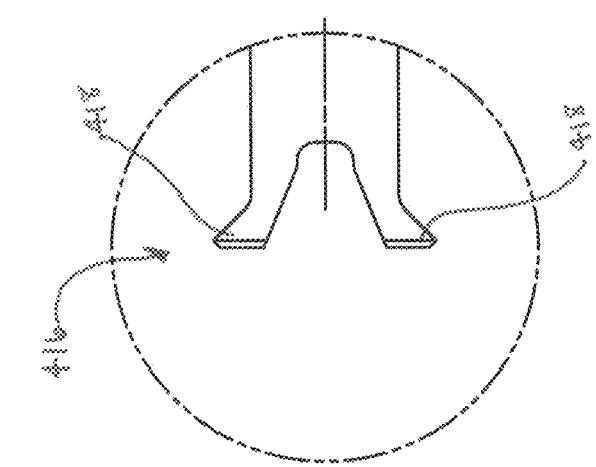
FIG. 4I a partial end view of an example inner cannula.
Figure 4J:
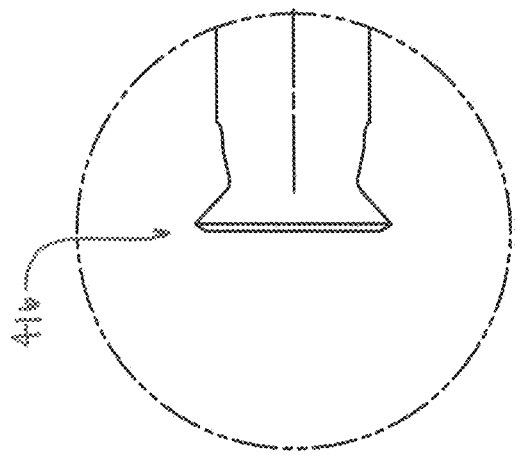
FIG. 4J a partial end view of an example inner cannula.

The inner cannula 104 may also include an attachment feature 416 for mating with a corresponding connector 700. An end view of an example attachment feature 416 is provided in FIG. 4H. FIG. 4I provides a side view of an example attachment feature 416 and FIG. 4J provides a top/bottom view of an example attachment feature 416. As illustrated in FIGS. 4H-4J, the attachment feature 416 may be located at the proximate end 406 of the inner cannula 104 and may include two projections 418 extending from the inner cannula 104. The projections 418 may be formed from the body surface of the inner cannula 104. In an alternate example, the projections 418 are attached or otherwise joined to the proximate end 406 of the inner cannula 104.

Figure 5:
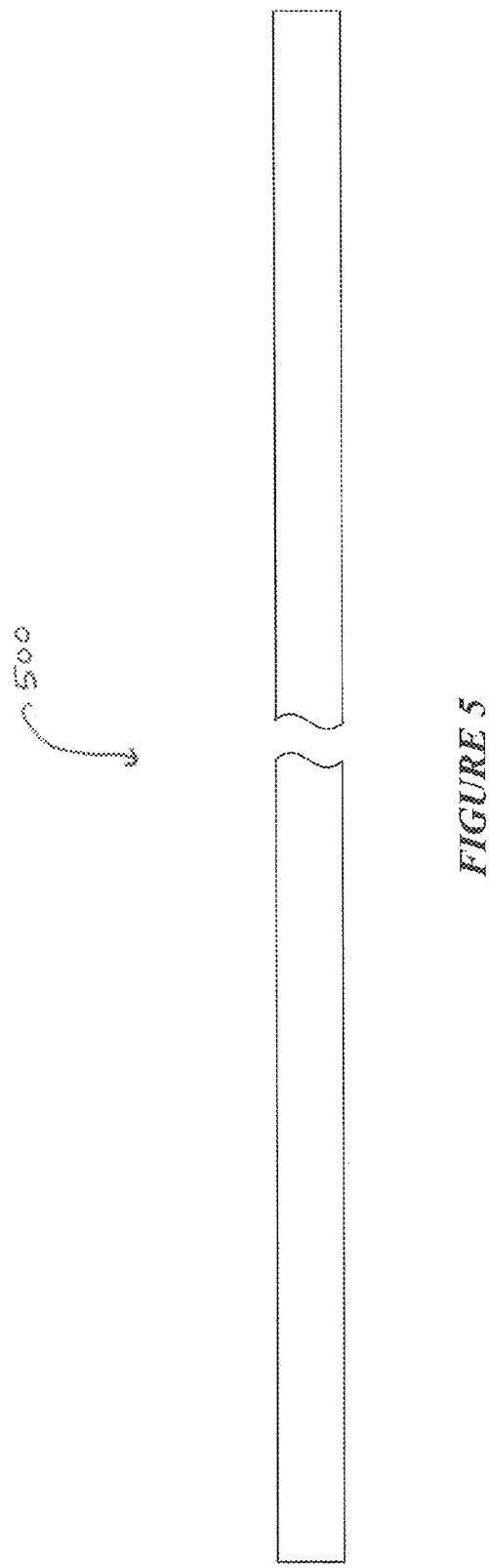
FIG. 5 is a top view of an example sealing lumen.

FIG. 5 provides a top view of an example sealing lumen 500. The sealing lumen 500 is sized and configured to cover inner cannula 104. The sealing lumen 500 may cover the entire length of the inner cannula 104 or only a portion of the inner cannula 104. The sealing lumen 500 may provide a barrier between the inner cannula 104 and the outer cannula 102. For example, the sealing lumen 500 may prevent liquids or other substances present in the central lumen 302 of the outer cannula 102, via grooves 312, for example, from entering the central lumen 402 of the inner cannula 104. The sealing lumen 500 may also prevent any liquid or other substance present in the central lumen 402 of the inner cannula 104 from entering the central lumen 302 of the outer cannula 102. For example, the sealing lumen 500 may prevent injection material, such as bone cement, present in the central lumen 402 of the inner cannula 104, from entering the central lumen 302 of the outer cannula 102.

The sealing lumen 500 may provide an impermeable or permeable barrier. An example sealing lumen 500 may comprise a heat shrink polymer. For example, the sealing lumen 500 may be comprised of a biocompatible heat shrink tubing. The sealing lumen 500 may seal around and over the distal end 408 of the inner cannula 104. In another example, the sealing lumen 500 may be tube-shaped and provide an opening at the distal end 408 of the inner cannula 104 such that the sealing lumen 500 seals around the perimeter of the distal end 408 of the inner cannula 104 but not over the end portion.

Figure 6A:
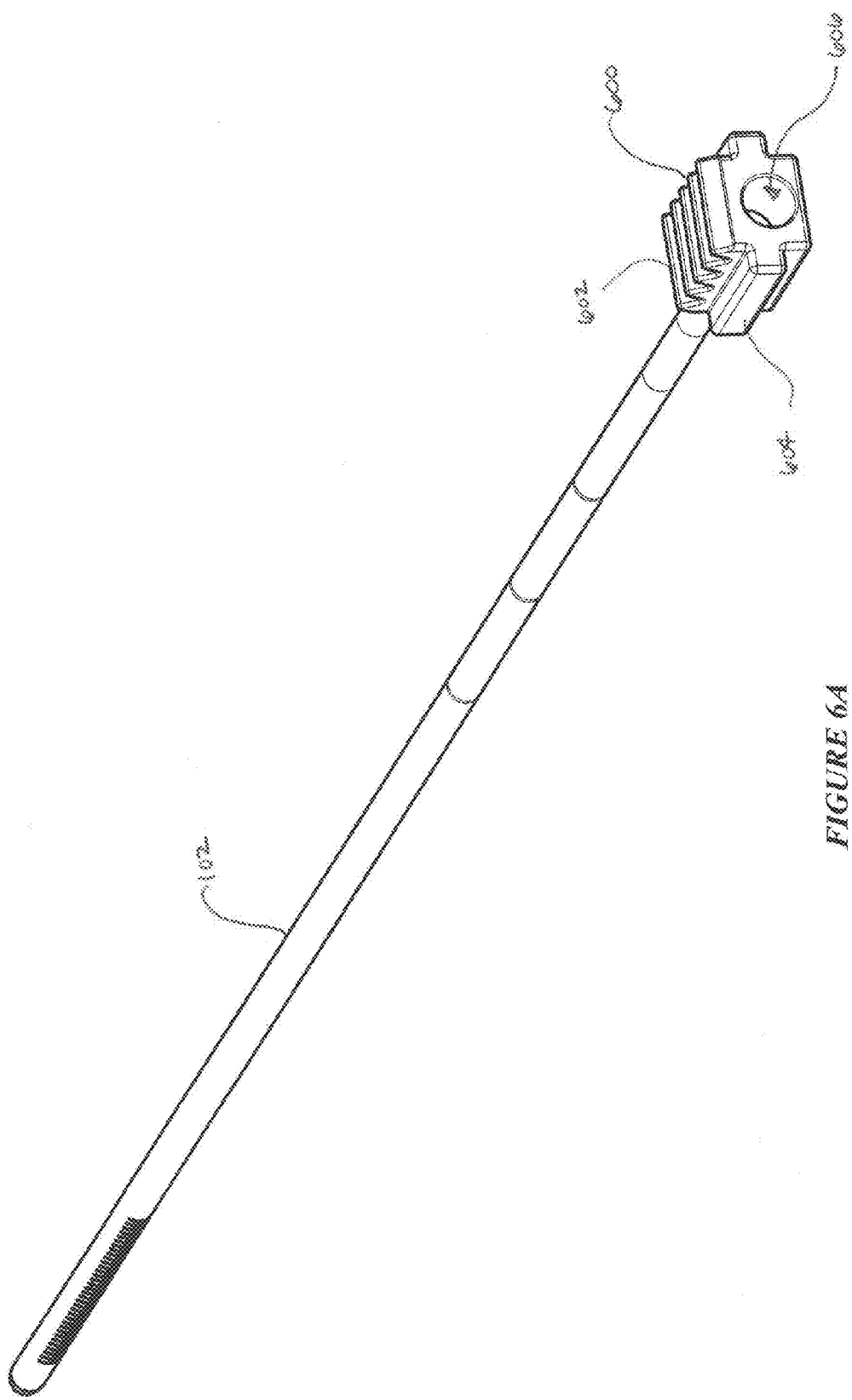
FIG. 6A is a perspective view of an example outer cannula with connector.
Figure 6B:
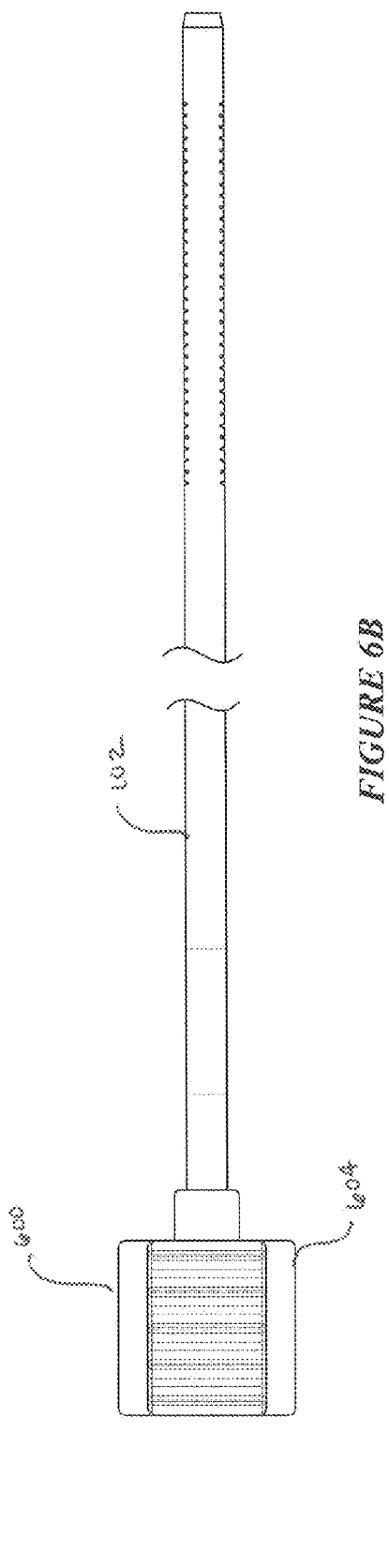
FIG. 6B is a top view of an example connector.
Figure 6C:
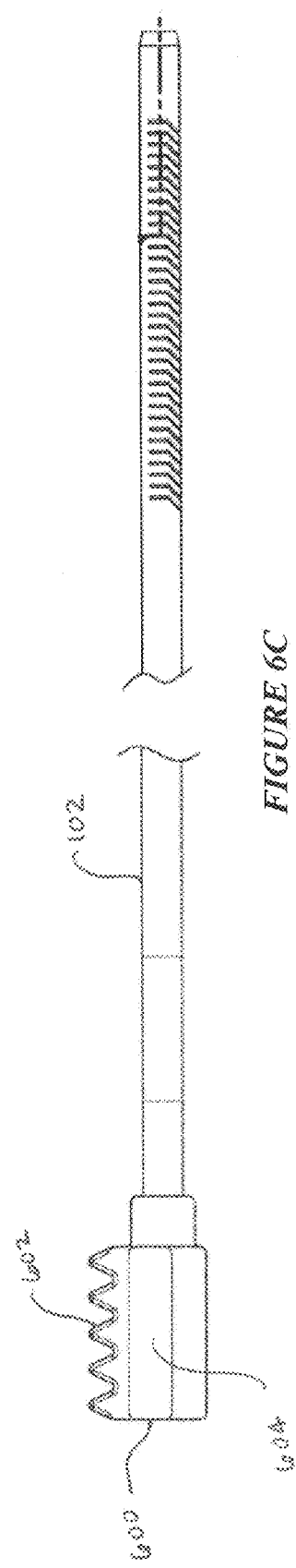
FIG. 6C is a side view of an example connector.

Each of the outer cannula 102 and the inner cannula 104 are associated with a connector. For example, as illustrated in FIGS. 6A-6C, the proximal end 306 of the outer cannula 102 may be coupled to a geared connector 600. The geared connector 600 may include gear teeth 602 sized and configured to engage corresponding feature associated with the handle 106. For example, the gear teeth 603 may engage corresponding teeth of a ratchet assembly 1010 associated with the handle 106. As a result, a force applied to the gear teeth 602 results in a corresponding movement in the geared connector 600 and the outer cannula 102.

Figure 6D:
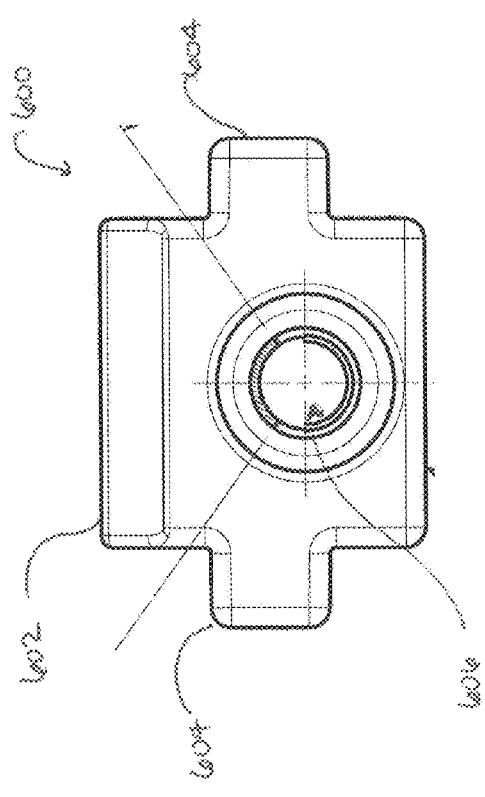
FIG. 6D is an end view of an example connector.

The geared connector 600 may include a feature for engaging an interior surface of the handle 106. For example, as illustrated in FIG. 6D, the geared connector 600 may include a projection 604 extending from opposite sides of the geared connector 600. In an alternate embodiment (not shown), the geared connector 600 may include recesses on opposite sides of the geared connector 600. In a further example (not shown), the geared connector 600 may include additional or fewer projections 604 (or recesses) extending from the same or multiple surfaces of the geared connector 600. The projection 604 (or recess) may be sized and configured to engage an interior surface of the handle 106. The projection 604 (or recess) may contact an interior surface of the handle 106 to prevent rotation of the geared connector 600 and the outer cannula 102. The projection 604 (or recess) may also contact an interior surface of the handle 106 to provide a guide for movement of the geared connector 600 within the handle 106.

Figure 6E:
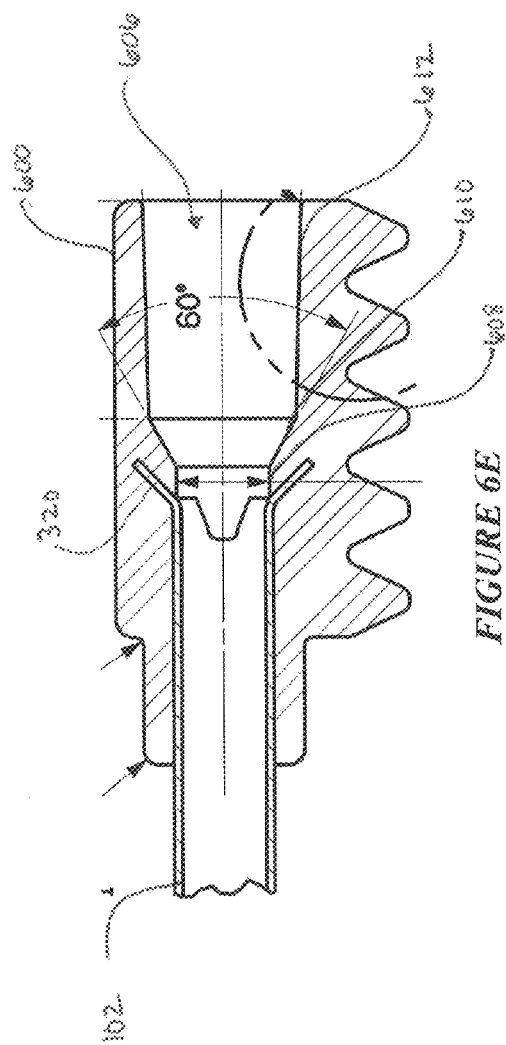
FIG. 6E is a cross-section view of an example connector.

FIG. 6E provides a cross-section view of the example geared connector 600. As illustrated in FIG. 6E, and as outlined above, the geared connector 600 may be coupled to the outer cannula 102 at an attachment feature 320.

The geared connector 602 may also include a central lumen 606 extending through the body of the geared connector 602 in the longitudinal direction. The end profile of the central lumen 606 may define any suitable shape including, for example, circular, elliptical, square, rectangular, or any other regular or irregular shape. For example, as illustrated in FIG. 6D, the end profile of the example central lumen 606 may define a circular shape. Likewise, the longitudinal profile of the central lumen 606 may define any suitable regular or irregular shape. For example, as illustrated in FIG. 6E, the example central lumen 606 may include a first portion 608, a tapered portion 610, and a second portion 612. The first portion 608 may have a diameter sized and configured to accommodate a surgical instrument. The diameter of the first portion 608 may be sized and configured to correspond to the diameter of the central lumen of the 302 of the outer cannula 102. As illustrated in FIG. 6E, the diameter of the first portion 608 is similar to the diameter of the central lumen of the 302. The second portion 612 may have a diameter larger than the diameter of the first portion 608. In another example, the second portion 612 may have a diameter sized and configured to accommodate a portion of a connector 700 associated with the inner cannula 104. The first portion 608, tapered portion 610 and the second portion 612 may be sized and configured to guide the placement of the inner cannula 104 into the outer cannula 102. In another example the central lumen 606 may include a luer taper. In an alternate example, the central lumen 606 may include a constant diameter.

Figure 7A:
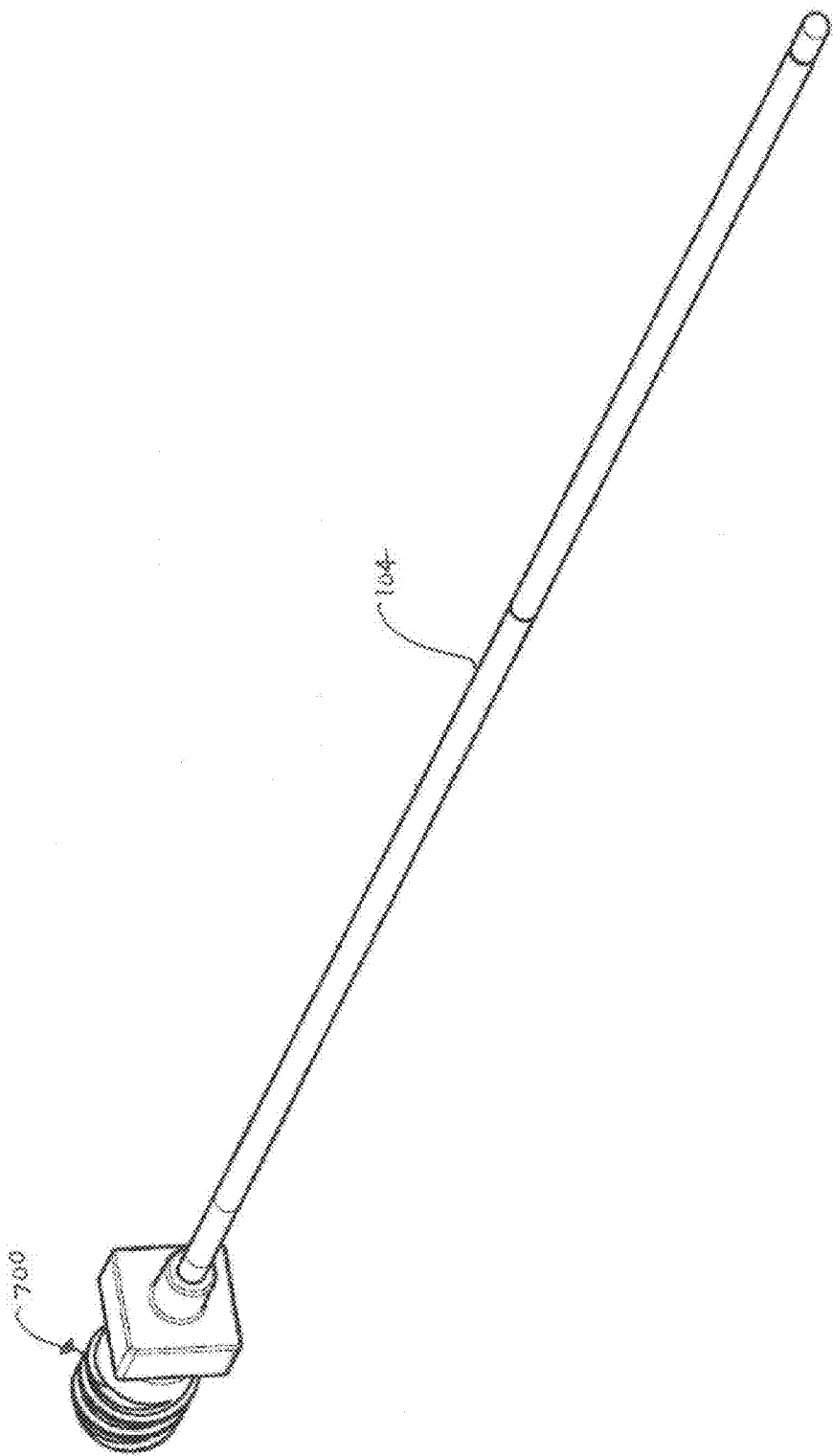
FIG. 7A is a perspective view of an example connector.

The inner cannula 104 may also be coupled to a connector. For example, as illustrated in FIGS. 7A-C, the proximal end 406 of the inner cannula 104 may be coupled to a threaded connector 700. The threaded connector 700 may include a body portion 702 having threads 704 sized and configured to releaseably engage a corresponding surgical instrument. For example, the threaded connector 700 may be sized and configured to engage a cement delivery and/or injectable therapy delivery tool. An example body portion 702 may include a single-start thread, double-start threads, a buttress thread, an acme thread, a pipe thread, a square thread, or any other style of thread known in the art. In an alternate example, the threaded connector 700 may include other features for coupling with a medical instrument including, for example, press fit, taper fit, bonding fit with the use of an adhesive, expansion fit, and mechanical interlocking fit, such as, a bayonet connection.

The threaded connector 700 may also include a feature for engaging a surface of the handle 106. For example, the threaded connector 700 may engage a body portion 1002 of the handle 106 to fix the location of the threaded connector 700 with respect to the steerable cannula assembly 100. An example threaded connector 700 may include a recess 706 and a collar 708 located on the body portion 702. The recess 706 and the collar 708 may be sized and configured to engage a body portion 1002 of the handle 106. The body portion 1002 of the handle may include an interior and/or an exterior surface of the handle 106. For example, as illustrated in FIG. 10C, the recess 706 and the collar 708 are sized and configured to engage a corresponding portion of the body portion 1002 of the handle 106.

The collar 708 of the threaded connector 700 may also be sized and configured for engaging an interior surface of the handle 106. For example, the end profile of the collar 708 may define any suitable shape including, for example, circular, elliptical, square, rectangular, or any other regular or irregular shape that is configured to engage an interior surface of the handle 106. As illustrated in FIG. 7D, the end profile of the collar 708 can define a square shape sized to engage an interior surface of the handle 106 to prevent rotation of the threaded connector 700 and the inner cannula 104.

FIG. 7E provides a cross-section view of the example threaded connector 700. As illustrated in FIG. 7E, and as outlined above, the threaded connector 700 may be coupled to the inner cannula 104 at an attachment feature 416. The threaded connector 700 may include a central lumen 710 extending through the body of the threaded connector 700 in the longitudinal direction. The end profile of the central lumen 710 may define any suitable shape including, for example, circular, elliptical, square, rectangular, or any other regular or irregular shape. For example, as illustrated in FIG. 7D, the end profile of the central lumen 710 may define a circular shape. Likewise, the longitudinal profile of the central lumen 710 may define any suitable regular or irregular shape. For example, as illustrated in FIG. 7E, the example central lumen 710 may include a first portion 712, a tapered portion 714, and a second portion 716. The first portion 712 may have a diameter sized and configured to accommodate a surgical instrument. The diameter of the first portion 712 may be sized and configured to correspond to the diameter of the central lumen of the 402 of the inner cannula 104. As illustrated in FIG. 7E, the diameter of the first portion 712 is similar to the diameter of the central lumen of the 402. The second portion 716 may have a diameter larger than the diameter of the first portion 712. The first portion 712, tapered portion 714, and the second portion 716 may be sized and configured to provide an advantageous flow property of an injection material, such as bone cement, introduced into the central lumen 402 of the inner cannula 104. In another example the central lumen 710 may include a luer taper. The first portion 712, tapered portion 714, and the second portion 716 may also be sized and configured to guide the placement of the surgical instrument into the inner cannula 104. In an alternate example, the central lumen 710 may include a constant diameter.

Figure 8A:
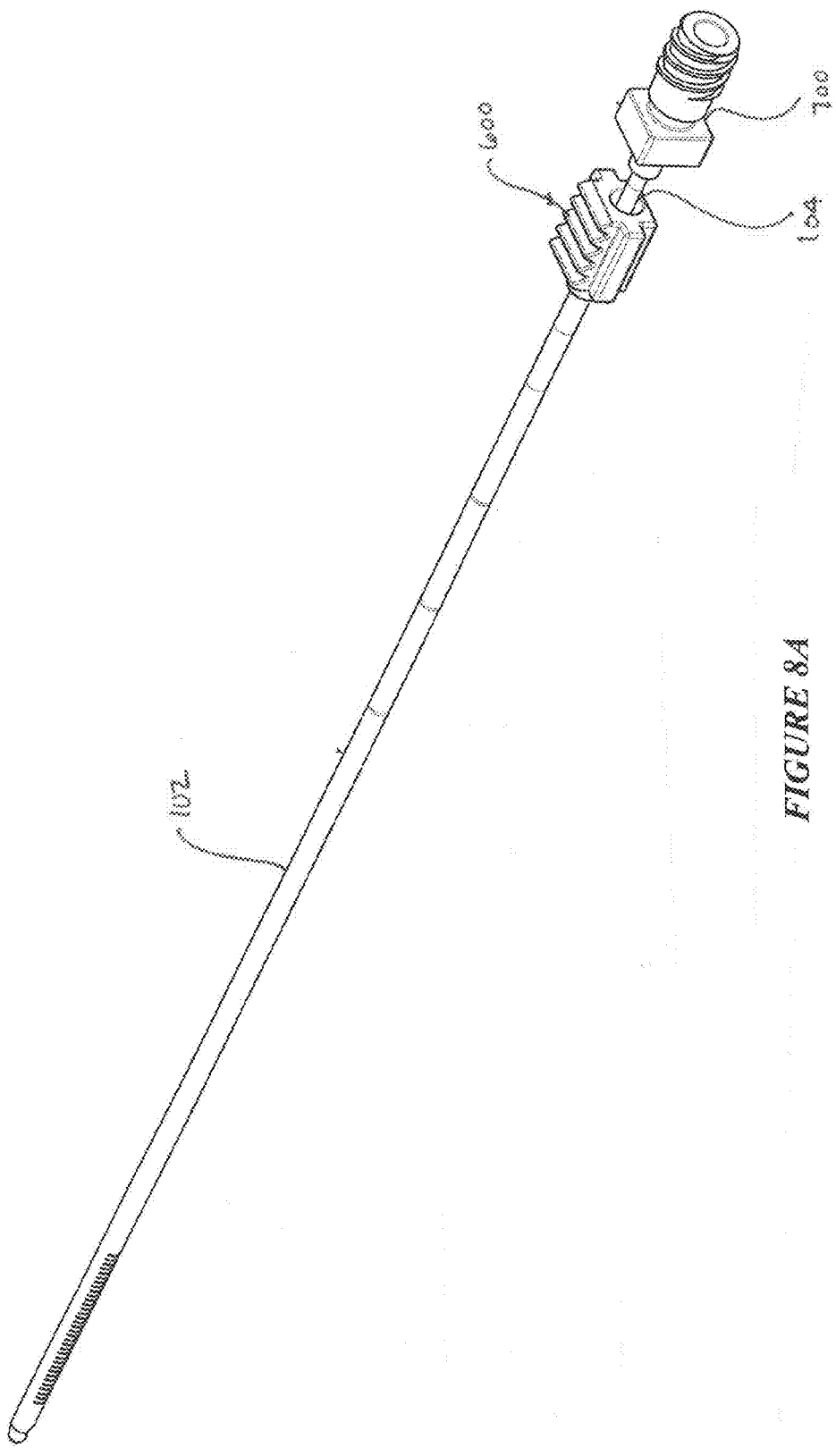
FIG. 8A is a perspective view of an example assembled outer cannula and inner cannula.
Figure 8B:
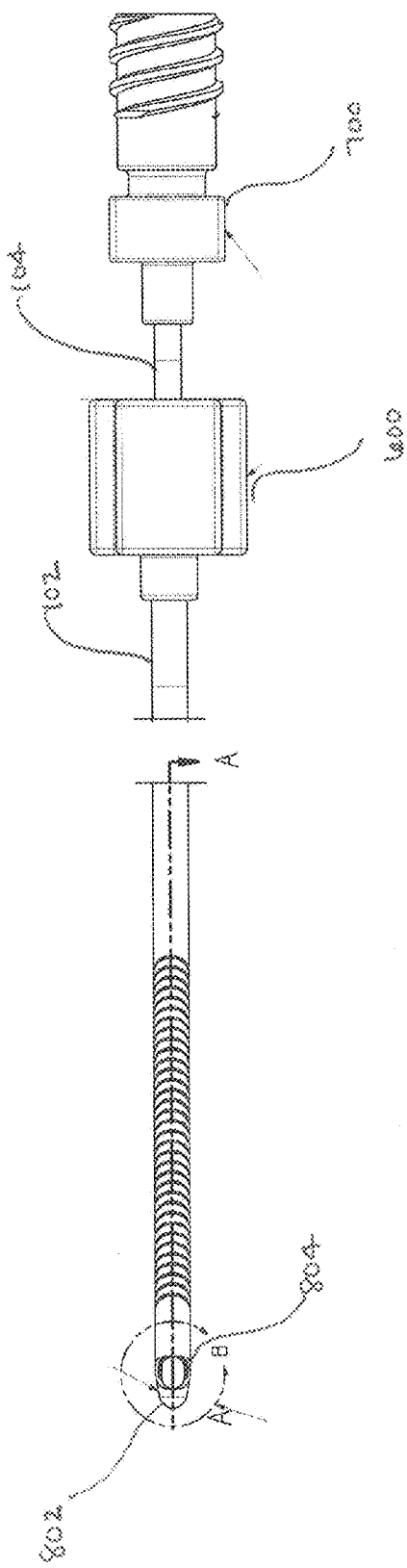
FIG. 8B is a top view of an example assembled outer cannula and inner cannula.
Figure 8C:
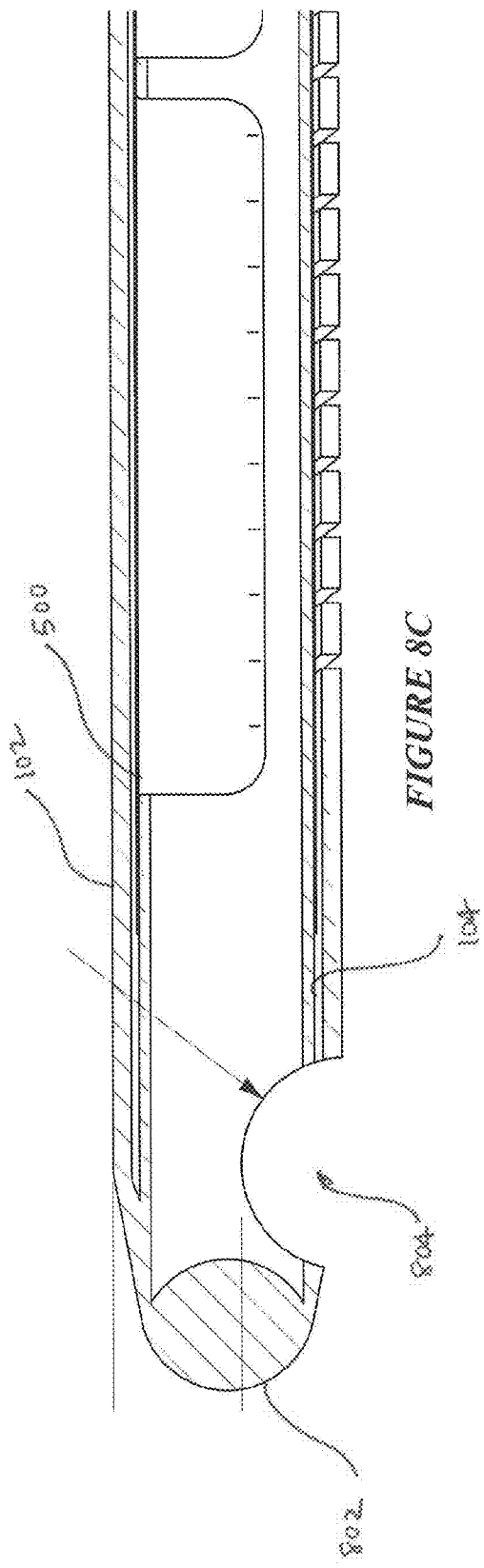
FIG. 8C is a partial cross-section view of an example assembled outer cannula and inner cannula.

FIG. 8A provides a perspective view of an assembled outer cannula 102, sealing lumen 500, and inner cannula 104. As illustrated, the sealing lumen 500 is provided over the inner cannula 104. The combined sealing lumen 500 and inner cannula 104 are located within the central lumen 302 of the outer cannula 102. The distal end 408 of the inner cannula 104 may be coupled to the distal end 308 of the outer cannula 102. For example, the inner cannula 104 and the outer cannula 102 may be coupled via a chemical bond, a thermal bond, and/or a mechanical bond. Example bonding techniques may include, for example, a weld, a threaded connection, a press fit connection, a taper fit connection, an expansion fit connection, a solder, adhesive bonding, and a mechanical interlocking fit such as a bayonet connection. As illustrated in FIG. 8B, the inner cannula 104 and the outer cannula 102 may be coupled by a spot weld 802. FIG. 8C provides a partial cross-section view of an assembled outer cannula 102, sealing lumen 500, and inner cannula 104. As illustrated, the spot weld 802 provides a permanent mechanical coupling of the outer cannula 102 and the inner cannula 104. As a result, the distal ends of the respective outer cannula 102 and inner cannula 104 are fixed with respect to each other.

The assembled outer cannula 102, sealing lumen 500, and inner cannula 104 may also include an opening 804. The opening 804 may provide access to the central lumen 402 of the inner cannula 104. That is, the opening 804 may provide a delivery port for providing a tool, implant, or filler material to an interior vertebral body.

Figure 9A:
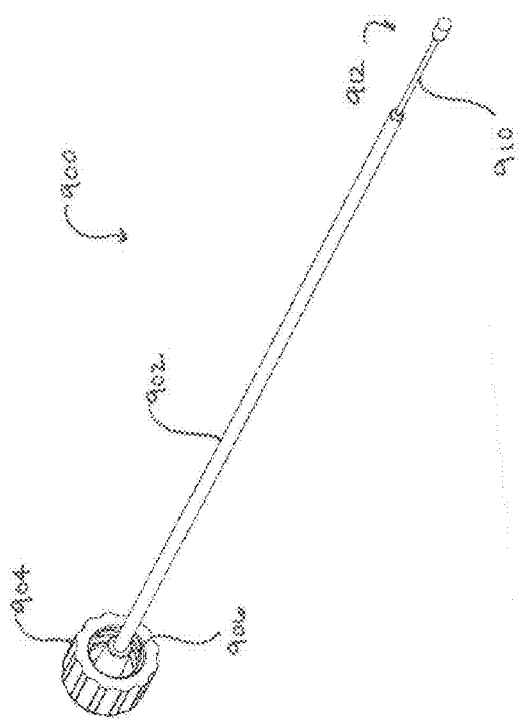
FIG. 9A is a perspective view of an example stylet.
Figure 9B:
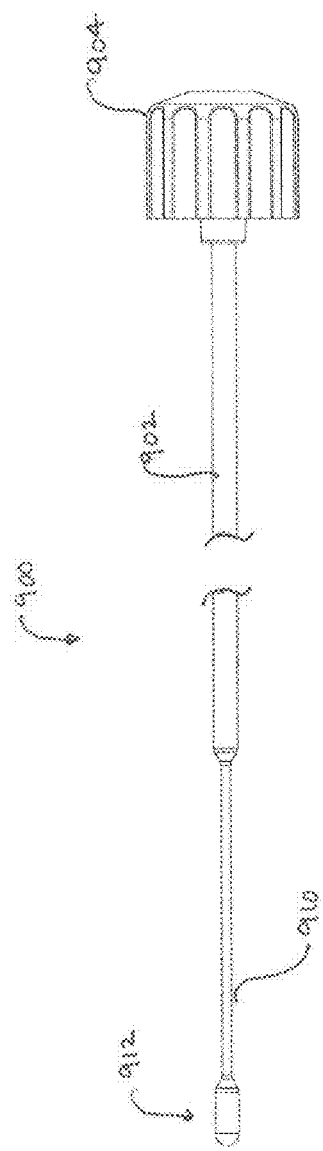
FIG. 9B is a top view of an example stylet.

FIG. 9A provides a perspective view of a stylet 900. The stylet 900 can include a body portion 902 and a stylet overmold 904. The body portion 902 may be sized and configured to be received within the central lumen 402 of the inner cannula 104. The stylet 900 may be used to prevent bone, blood, or other interstitial fluid/materials from clogging the opening 804 during insertion. The body portion 902 may be comprised of a flexible biocompatible material. The stylet overmold 904 may include engagement portion 906 configured to engage the corresponding feature on the threaded connector 700. For example, the engagement portion 906 may include threads configured to matingly engage threads 704 of the threaded connector 700.

The stylet 900 may also include a flexible portion 910 extending along the longitudinal axis of the body portion 902. The flexible portion 910 may be sized and located to provide flexibility to the stylet 900. The flexible portion 910 may include a diameter less than the diameter of the body portion 902. The flexible portion 910 may be located proximate the distal end 912 of the body portion 902. An example flexible portion 910 may be sized and located on the body portion 902 at a location to correspond to the articulating portion 310 of the outer cannula 102 when the stylet 900 is inserted into the central lumen 402 of the inner cannula 104. In a further example, the flexible portion 910 may be located at any portion along the body portion 902.

Figure 10A:
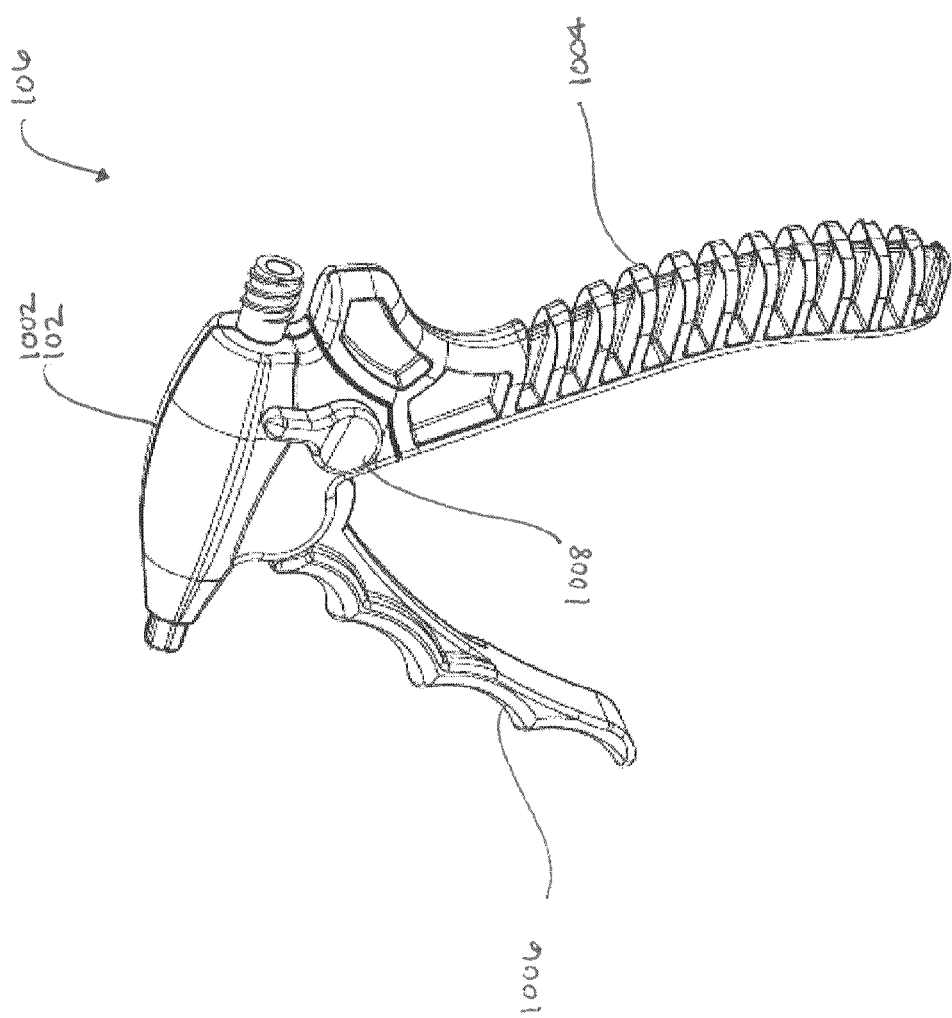
FIG. 10A is a perspective view of an example handle.
Figure 10B:
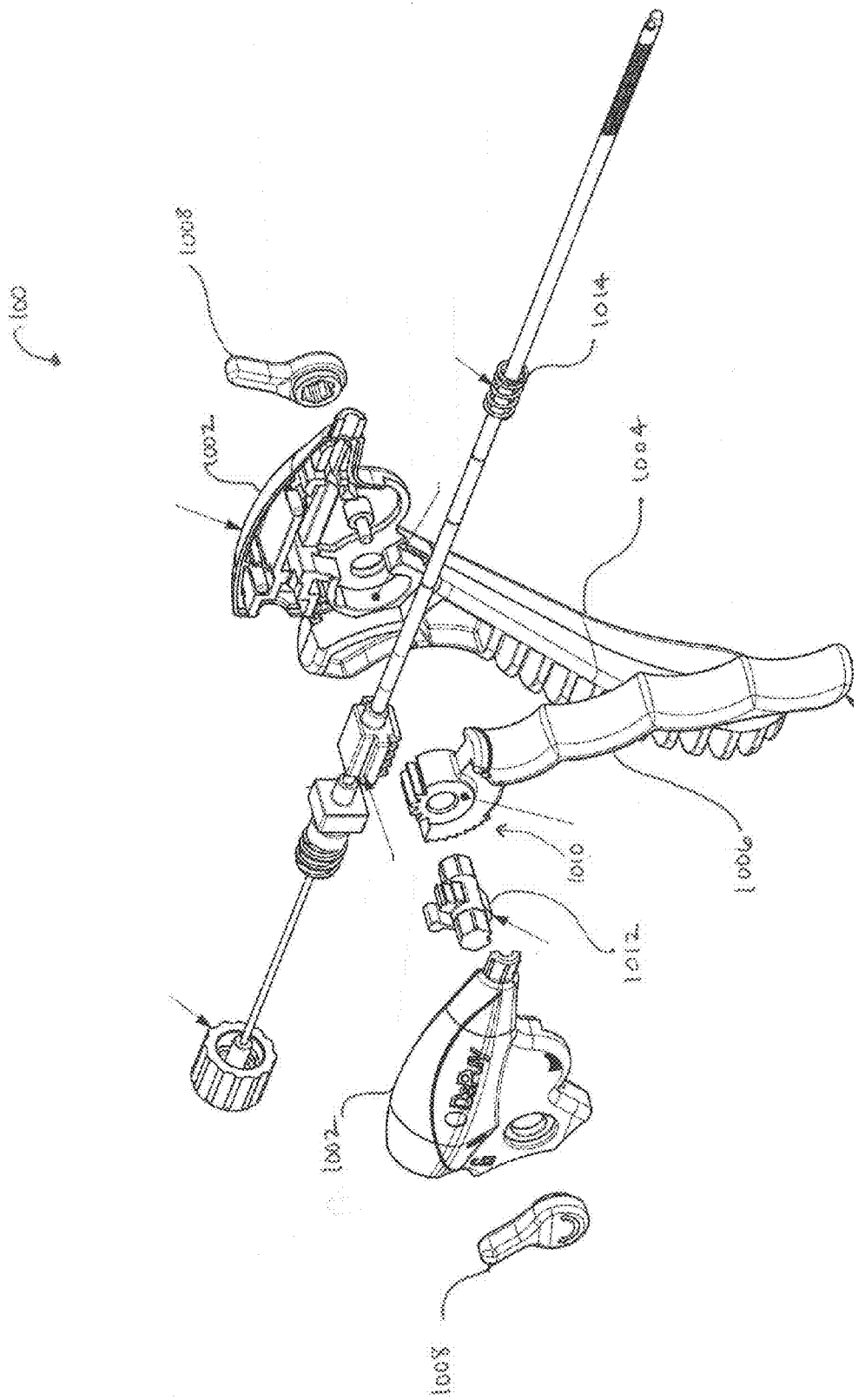
FIG. 10B is an exploded view of an example steerable cannula assembly.
Figure 10C:
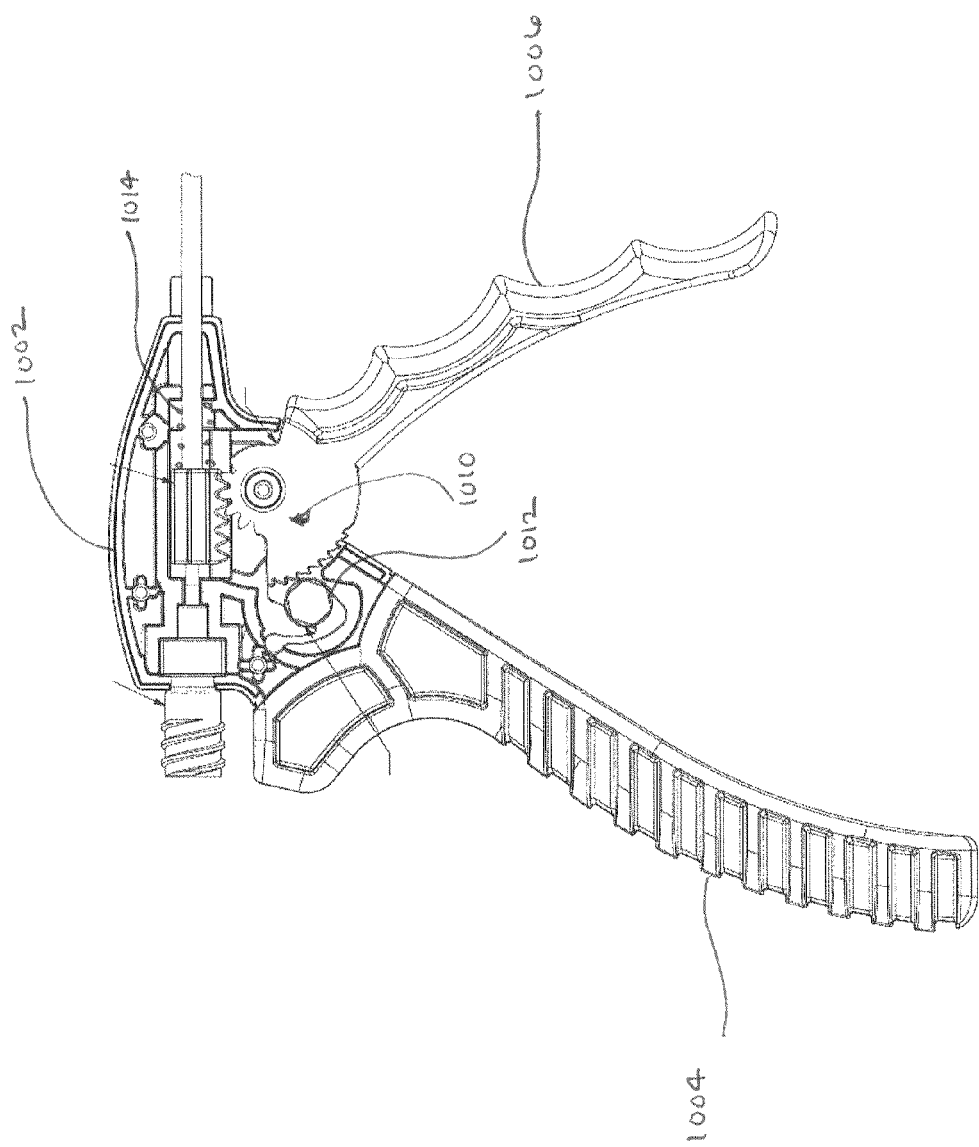
FIG. 10C is a cross-section view of an example steerable cannula assembly.

FIG. 10A provides a perspective view of an example handle 106. The handle 106 may be operably coupled to the outer cannula 102 and the inner cannula 104. The exterior of the handle 106 may include a body portion 1002, a grip 1004, a lever 1006, and a ratchet release 1008. FIG. 10B provides an exploded view of an example steerable cannula assembly 100. FIG. 10C provides a cross-section view of an example steerable cannula assembly 100. As illustrated in FIG. 10C, the threaded connector 700 is fixedly engaged to the body portion 1002 such that the longitudinal movement of the inner cannula 104 is fixed with respect to the body portion 1002.

Figure 10D:
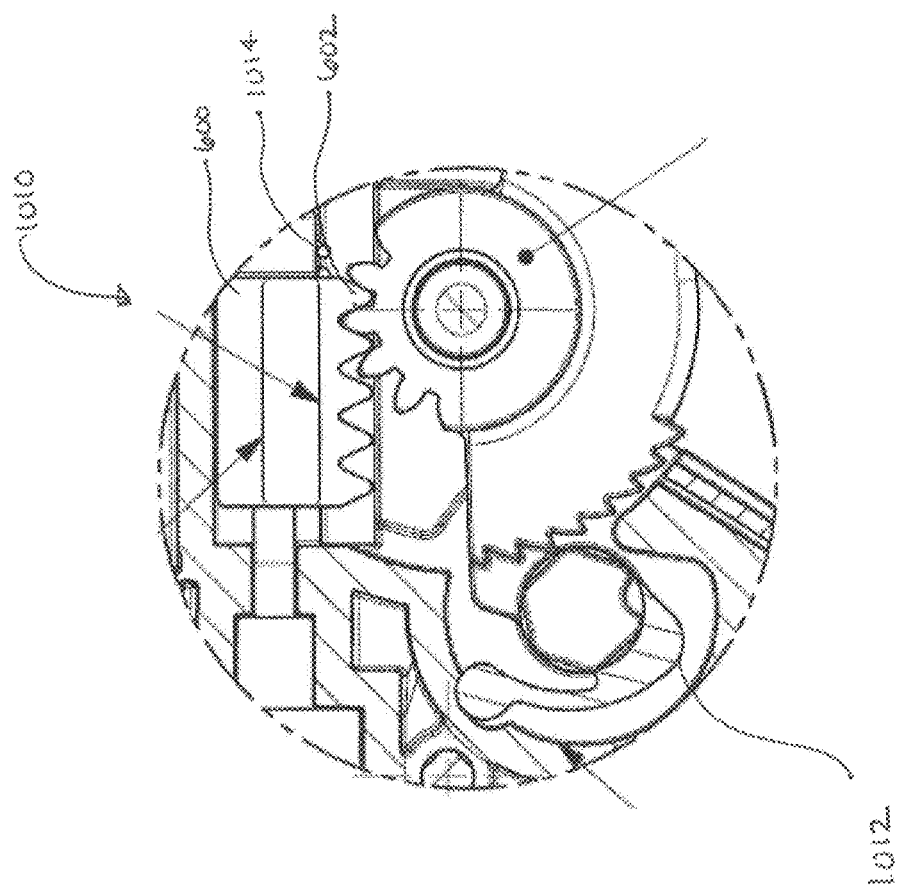
FIG. 10D is a partial cross-section view of an example steerable cannula assembly.

As illustrated in FIGS. 10B and 10C, the handle 106 further includes a ratchet assembly 1010 for applying force to the corresponding gear teeth 602 of the geared connector 600. FIG. 10D provides a partial cross-sectional view of the example ratchet assembly 1010. As the user depresses the lever 1006 the gear teeth associated with the ratchet assembly 1010 located on the lever 1006 engage the corresponding gear teeth 602 on the geared connector 600 to move the outer cannula 102 in a direction along the longitudinal axis. The ratchet assembly 1010 also includes a spring pawl 1012 coupled to the ratchet release 1008 configured to provide a locking/unlocking mechanism to the ratchet. The ratchet assembly 1010 may also include a compression spring 1014. The compression spring 1014 may be located along the outer cannula 102 between the body portion 1002 and the geared connector 600 and configured to provide a return pressure on the ratchet assembly 1010. It is contemplated that the example lever 1006 and ratchet assembly 1010 may be motorized or otherwise automated.

In operation, the steerable cannula assembly 100 is used by inserting the outer cannula 102 and inner cannula 104, coupled together as described above, into an interior body, such as vertebral body. The user manipulates the handle 106 to selectively adjust the articulating portion 310, and the interior body is augmented, either by the movement/placement of the outer cannula 102/inner cannula 104 itself or by a tool/material passed through cannula assembly. The cannula assembly can then be withdrawn from the interior body.

The articulating portion 310 can be selectively adjusted in response to user's manipulation of the handle 106/lever 1006. In response to movement of the lever 1006, a corresponding force is applied to the outer cannula 102 via the variable action of the ratchet assembly 1010. The ratchet assembly 1010 engages the outer cannula 102 at the geared connector 600. The geared connector 600 is moved in the direction of the longitudinal axis 304 of the outer cannula 102, as a result, the force applied to the outer cannula 102 at the connector 600 is also along the longitudinal axis 304. Because the distal ends of the outer cannula 102 and the inner cannula 104 are joined together, movement of the proximal end 306 of the outer cannula 102 in conjunction with the fixed location of the proximal end 406 of the inner cannula 104 with respect to the steerable cannula assembly 100 (between the threaded connector 700 and the body portion 1002), results in bending/curvature of the articulating portion 310.

As the geared connector 600 and the outer cannula 102 move along the longitudinal axis 304, the width of the grooves 312 increase or decrease. For example, as the handle 106 is depressed, the outer cannula 102 is moved along the longitudinal axis 304 in a direction opposite the distal end 308, and the width of the grooves 312 decreases. As the width of the grooves 312 decreases, the interlocking portion 318 of the projections 314 engage thereby preventing further curvature of the articulating portion 310. When each of the interlocking portion 318 are fully engaged the steerable cannula assembly 100 is considered in a fully curved and/or articulated position. As the articulating portion 310 of the outer cannula 102 curves/articulates, the inner cannula 104 bends/flexes within the outer cannula 102. In an example steerable cannula assembly 100, the slots 410 extending along the longitudinal axis 414 of the inner cannula 104 provide the flexation point for the inner cannula 104.

Figure 11A:
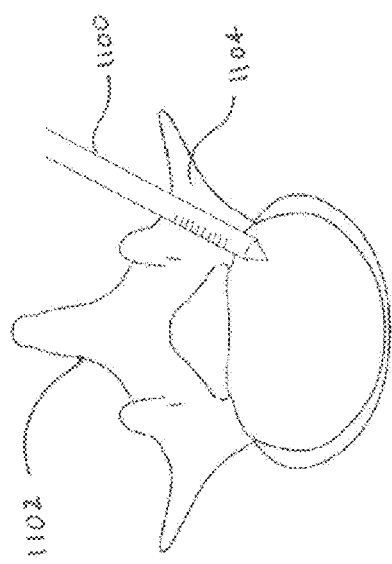
FIGS. 11A-11E are an example steerable cannula assembly and vertebral body.

As illustrated in FIG. 11A, the outer cannula 102 and the inner cannula 104 as assembled (hereafter referred to as "cannula assembly 1100") can be inserted through the pedicle 1104 of a vertebrae 1102 and into the interior of the vertebral body 1102. In an alternate example (not shown), the cannula assembly 1100 can be inserted into the interior body via uni-transpedicular access and/or bi-pedicular access.

Figure 11B:
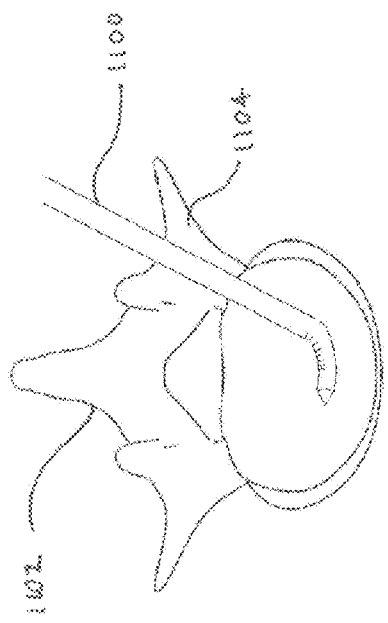

As illustrated in FIG. 11B, the cannula assembly 1100 may be inserted into the vertebral body 1102 to create a cavity/treatment site 1106. For example, the user can manipulate the handle 106 to tamp the end of the cannula assembly 1100 into the cancellous bone. Similarly, the user may manipulate the handle 106/lever 1006 to selectively adjust the articulating portion 310 and thereby impact the cancellous bone as the cannula assembly 1100 curves/bends within the interior body.

Figure 11C:
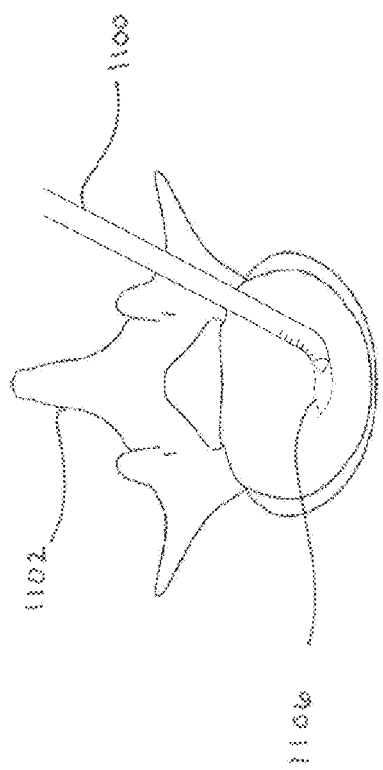

As illustrated in FIG. 11C, as the cannula assembly 1100 is withdrawn, the cavity 1106 becomes accessible for the delivery of a treatment element. If a stylet 900 is utilized during initial insertion and/or cavity creation, it may be removed before the treatment element is delivered to the interior body. The treatment element may be delivered to the cavity 1106 via the central lumen 402 of the inner cannula 104 and the opening 804 in the cannula assembly 1100. The treatment element can include, for example, a filler material and/or an inflatable body, such as those used for kyphoplasty. The filler material can include, for example, bone cement, bone chips, demineralized bone, and/or an implant. By creating the cavity 1106 before delivery of the filler material, the user is able to control the placement and flow of the filler material and limit material extravagation. The user can also symmetrically fill the vertebral body 1102.

Figure 8D:
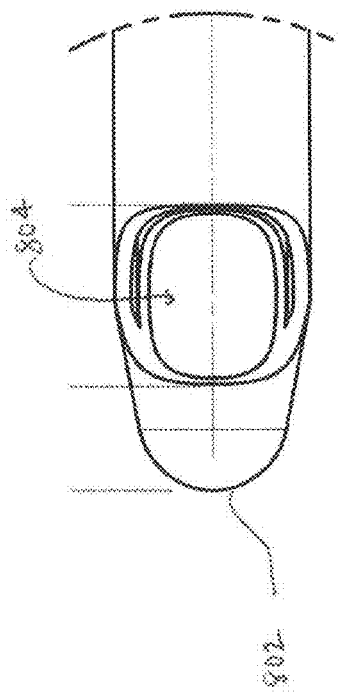
FIG. 8D is a partial view of an assembled outer cannula and inner cannula.
Figure 11D:
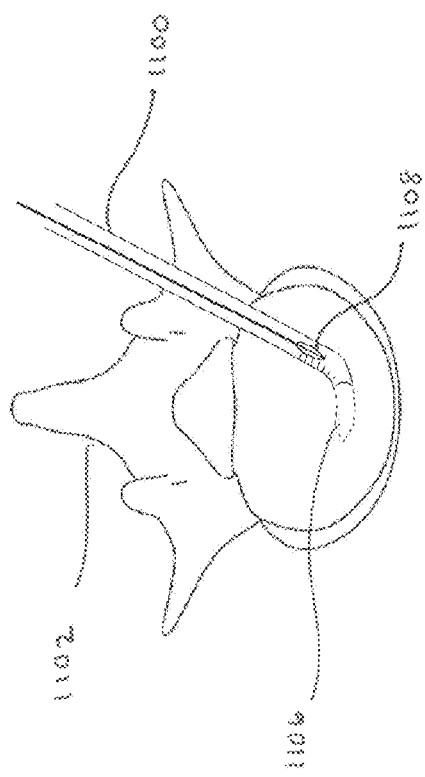
Figure 11E:
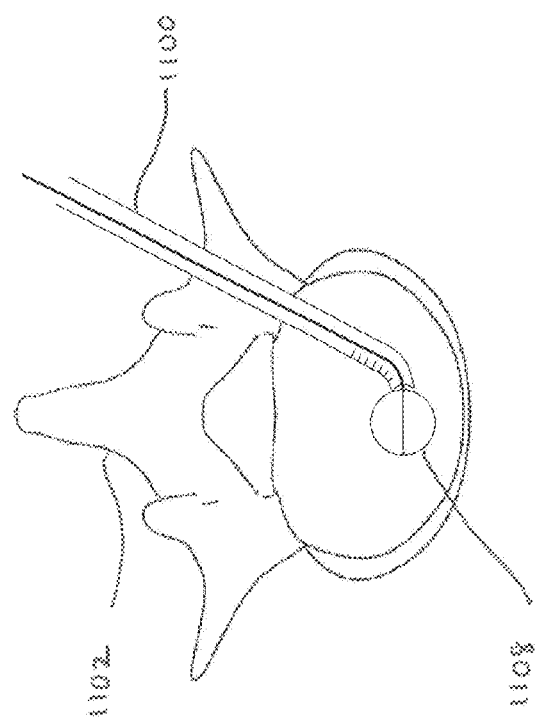

FIG. 11D illustrates the delivery of an inflatable body 1108, via the opening 804 in the cannula assembly 1100. As illustrated in FIG. 11D, the opening 804 can be located at the distal tip of the cannula assembly 1100. In an alternate example (see FIGS. 8B-8D), the opening 804 can be located on a side wall of the cannula assembly 1100. The inflatable body 1108 may be used to restore the height of a damaged vertebral body 1100 and restore lordosis. The inflatable body 1108 may also be used to aid in creation of the cavity/treatment site 1106. For example, as illustrated in FIG. 11E, the inflatable body 1108 may expand axially from the distal tip of the cannula assembly 1100 within the interior body thereby impacting the cancellous bone and creating and/or expanding the cavity 1106. The inflatable body 1108 may then be deflated and removed via the central lumen 401 of the inner cannula 104. Once the inflatable body 1108 has been removed, filler material may be applied to the cavity 1106. In a further example, the inflatable body 1108 may remain (deflated) within the cannula assembly 1100 and the filler material may be applied around the inflatable body 1108 to the cavity 1106.

Figure 12A:
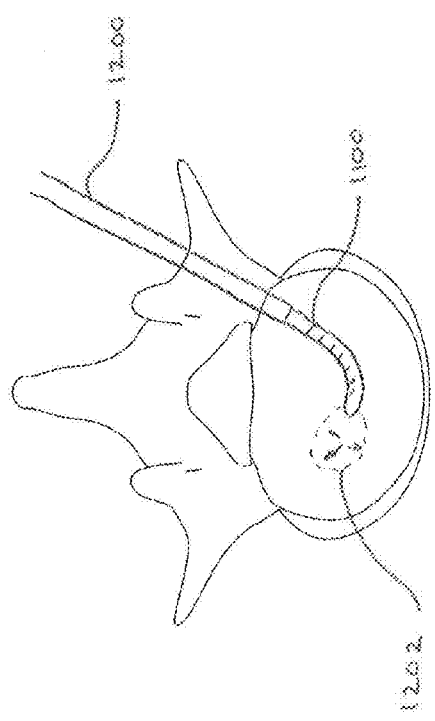
FIG. 12A is an example steerable cannula assembly and vertebral body.
Figure 12B:
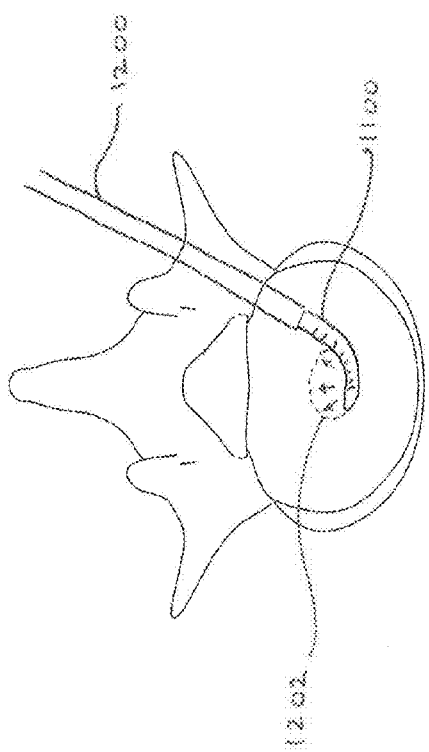
FIG. 12B is an example steerable cannula assembly and vertebral body.

In a further example, illustrated in FIG. 12A, the cannula assembly 1100 may be introduced into the patient's body and/or the vertebral body 1100 using an introducer cannula 1200. The distal end of the cannula assembly 1100 may extend through the end of the introducer cannula 1200 and into the interior body. An inflatable body 1202 may expand axially from the distal tip of the cannula assembly 1100 within the interior body thereby impacting the cancellous bone and creating and/or expanding the cavity. In an alternate embodiment, illustrated in FIG. 12B, the inflatable body 1202 may expand radially from the side of the cannula assembly 1100 to create the cavity.

Figure 13A:
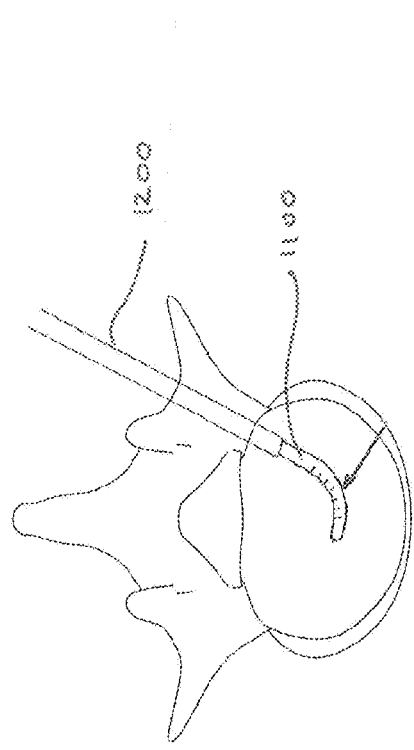
FIGS. 13A-13C are an example steerable cannula assembly and vertebral body.
Figure 13B:
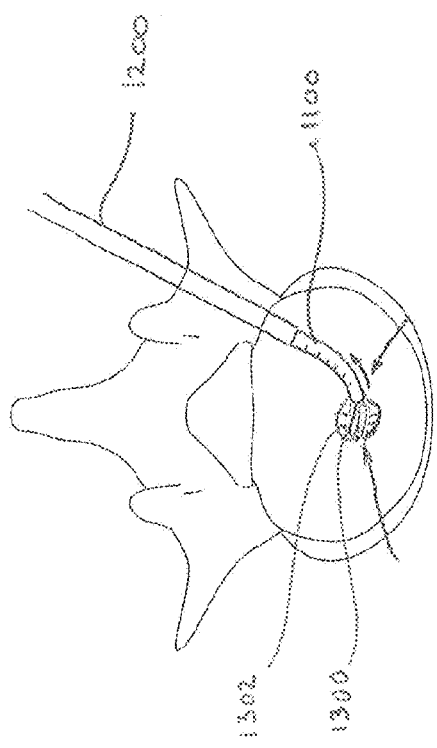
Figure 13C:
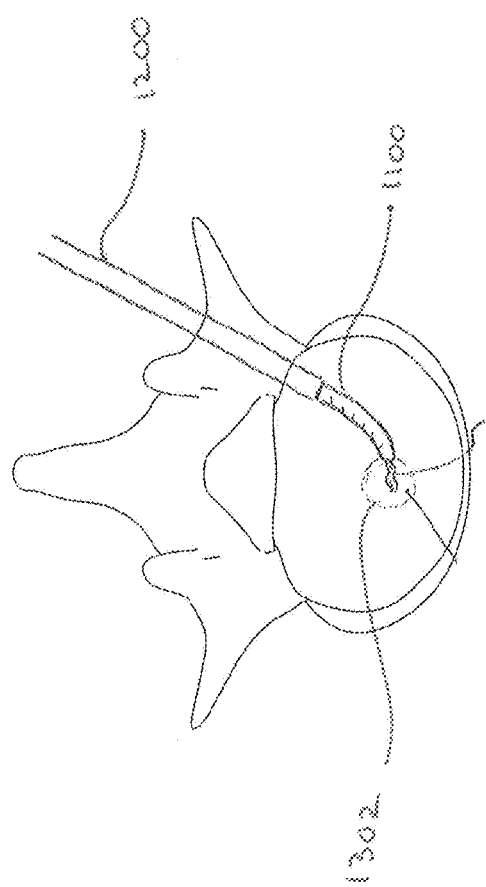

As illustrated in FIG. 13A, the cannula assembly 1100 may be "preloaded" with an inflatable body within the central lumen 402. As illustrated in FIG. 13B, once the distal tip of the cannula assembly 1100 is positioned within the internal body, the cannula assembly 1100 may retract to introduce the preloaded inflatable body 1300 into the cavity 1302. The preloaded inflatable body 1300 may be inflated within the interior body thereby impacting the cancellous bone and creating and/or expanding the cavity 1302. The preloaded inflatable body 1300 may then be deflated and removed via the central lumen 401 and filler material may be applied to the cavity 1302, as illustrated in FIG. 13C. Alternatively, the preloaded inflatable body 1300 may remain (deflated) within the cannula assembly 1100 and the filler material may be applied around the preloaded inflatable body 1300 to the cavity 1302.

In an alternate embodiment (not shown), a flexible drill may also be used to aid in creation of the cavity/treatment site 1106. The flexible drill may be delivered to the cavity 1106 via the opening 804 in the cannula assembly 1100.

After all treatment elements have been delivered to the cavity, the cannula assembly 1100, if still in a curved/articulated state, may be unlocked and returned to a normal, non-deflected state. The cannula assembly 1100 can then be removed from the interior body and the patient.

It should be noted that specific features of the various embodiments disclosed herein can be performed manually by user-applied forces or, alternately, utilizing specialized motors. For example, the actuating the lever 1106 and/or lateral movement of the geared connector 600 (and resultant movement of the outer cannula 102) can be performed manually by a surgeon who activates the lever 1106. Conversely, activating the lever 1106 and/or lateral movement of the geared connector 600 can be performed by motorized components that may utilize, in certain implementations, microprocessors or other guidance systems to coordinate the curving motion/articulation of the cannula assembly 1100 to optimally form the cavity within the target body and deliver the treatment element.

As will be readily appreciated by those of skill in the art, the various components described herein can be formed from a variety of biocompatible materials including, for example, metals such as cobalt chromium molybdenum (CoCrMo), cobalt chromium, titanium and titanium alloys, stainless steel or other metals. Other materials include, for example, composites, polymers, or ceramics. A coating may be added or applied to the various components described herein to improve physical or chemical properties, such as a plasma-sprayed titanium coating or Hydroxypatite. Moreover, skilled artisans will also appreciate that the various components herein described can be constructed with any dimensions desirable for implantation and cavity creation.

While the foregoing description and drawings represent examples of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed examples are, therefore, to be considered in all respects as illustrative and not restrictive, the scope of the invention being indicated by the appended claims and not limited to the foregoing description.

In addition, the various examples disclosed herein may be adapted for use in virtually any interior body region where the formation and/or augmentation of a cavity within tissue is required for a therapeutic or diagnostic purpose. While several examples are herein described with regard to treating bones, other examples can be used in other interior body regions as well. In addition, it is also anticipated that certain examples could be used for purposes other than medical, such as construction, manufacturing, and excavation, among others; accordingly, nothing herein is intended to limit application of the various examples to purely medical uses.

It will be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention, as defined by the following claims.

What is claimed is:

1. A steerable cannula assembly comprising:
    an outer cannula having a central lumen extending therethrough, the outer cannula including an articulating portion that curves in response to a force applied to a proximal end of the outer cannula;
    an inner cannula having a central lumen extending therethrough, the inner cannula being sized and configured to extend into a portion of the central lumen of the outer cannula, and coupled to a distal end of the outer cannula, wherein a tube-shaped sealing barrier covers at least a portion of an outer surface of the inner cannula;
    wherein the steering cannula assembly further includes an opening extending through a wall of the outer cannula and a wall of the inner cannula, the opening configured to provide access to the central lumen of the inner cannula.

2. The assembly of claim 1, wherein the inner cannula is coupled to the outer cannula at the distal end of the outer cannula by at least one of a chemical bond, a thermal bond, and a mechanical bond.

3. The assembly of claim 1, wherein the force applied to the proximal end of the outer cannula results in movement of the proximal end in a direction along a longitudinal axis of the outer cannula.

4. The assembly of claim 1, wherein the articulating portion includes a plurality of grooves and a plurality of corresponding projections, wherein at least two of the plurality of projections are sized and configured to interlock when the articulating portion is in a fully curved state.

5. The assembly of claim 1, wherein the inner cannula includes a slot extending along a longitudinal axis of the inner cannula.

6. The assembly of claim 5, wherein the inner cannula includes at least two slots extending along a longitudinal axis of the inner cannula,
    wherein a support member is provided between each of the slots, the support member comprising a ring-shaped portion extending in a direction perpendicular to the longitudinal axis of the inner cannula and having a having a central lumen extending therethrough.

7. The assembly of claim 1, further including a handle operably coupled to the outer cannula and the inner cannula, the handle including:
    a body portion fixedly engaged to a proximal end of the inner cannula;
    a ratchet assembly for applying the force to the proximate end of the outer cannula and moving the proximal end in a direction along the longitudinal axis of the outer cannula; and
    a lever operably coupled to the ratchet assembly.

8. The assembly of claim 7, further including a first connector coupled to a proximal end of the outer cannula, the first connector having a central lumen extending therethrough, and an outer surface sized and configured to matingly engage a ratchet assembly associated with the handle.

9. The assembly of claim 8, wherein the outer surface of the first connector includes a projection sized and configured to engage an interior surface of the handle.

10. The assembly of claim 7, further comprising a second connector coupled to a proximal end of the inner cannula, the second connector including a central lumen extending therethrough.

11. The assembly of claim 10, wherein the outer surface of the second connector includes a recess and a collar sized and configured to engage a body portion of a handle.

12. A method for treating a body using an steerable cannula assembly, the method comprising:
    inserting an articulating cannula into an interior body, the articulating cannula including an outer cannula and an inner cannula extending into a central lumen of the outer cannula, the outer cannula coupled to the inner cannula at their distal end, wherein a tube-shaped sealing barrier covers at least a portion of an outer surface of the inner cannula, and further wherein the steerable cannula assembly further includes an opening extending through a wall of the outer cannula and a wall of the inner cannula, the opening configured to provide access to the central lumen of the inner cannula;
    selectively adjusting the articulating cannula to cause a portion of the articulating cannula to curve;
    augmenting the interior body; and
    withdrawing the articulating cannula from the interior body.

13. The method of claim 12, wherein selectively adjusting the articulating cannula includes:
    maintaining a position of a proximal end of the inner cannula with respect to the steerable cannula assembly; and
    applying a force to the outer cannula in a direction along a longitudinal axis of the outer cannula.

14. The method of claim 12, wherein selectively adjusting the articulating cannula further includes:
    apply the force to the outer cannula such that a width of a plurality of grooves located on the outer cannula is decreased; and
    applying the force to the outer cannula such that a plurality of corresponding projections located on the outer cannula interlock when the articulating cannula is in a fully curved position.

15. The method of claim 12, wherein selectively adjusting the articulating cannula further includes:
    maintaining a position of the proximal end of the inner cannula such that a slot extending along a longitudinal axis of the inner cannula provides a flexation point for the inner cannula.

16. The method of claim 12, wherein selectively adjusting the articulating cannula further includes:
    coupling a ratchet assembly to the outer cannula such that variable action of the ratchet assembly corresponds to a complimentary force applied to the outer cannula.

17. The method of claim 12, further comprising:
providing a treatment element through the articulating cannula and into the interior body,
wherein the treatment element comprises at least one of an inflatable body and a filler material, the filler material comprising at least one of a bone cement, bone chips, demineralized bone, or an implant.

18. The method of claim 12, further comprising:
selectively adjusting the articulating cannula to create a cavity in the interior body.

19. The method of claim 12, further comprising:
inserting the articulating cannula through a pedicle of a vertebrae and into a body of the vertebrae.

20. The method according to claim 12, wherein the articulating cannula is introduced into the interior body via an introducer cannula, such that a distal end of the articulating cannula extends beyond a distal end of the introducer cannula and into the interior body.

* * * * *